US012105085B2

(12) United States Patent
Takeuchi et al.

(10) Patent No.: US 12,105,085 B2
(45) Date of Patent: Oct. 1, 2024

(54) BASE MATERIAL FOR MANUFACTURING SENSOR FOR ANALYZING DETECTION TARGET, SENSOR FOR ANALYZING DETECTION TARGET, METHOD FOR ANALYZING DETECTION TARGET

(71) Applicant: National University Corporation Kobe University, Kobe (JP)

(72) Inventors: Toshifumi Takeuchi, Kobe (JP); Yukiya Kitayama, Kobe (JP); Hirobumi Sunayama, Kobe (JP)

(73) Assignee: National University Corporation Kobe University, Kobe (JP)

( * ) Notice: Subject to any disclaimer, the term of this patent is extended or adjusted under 35 U.S.C. 154(b) by 273 days.

(21) Appl. No.: 16/617,987

(22) PCT Filed: May 18, 2018

(86) PCT No.: PCT/JP2018/019292
§ 371 (c)(1),
(2) Date: Nov. 27, 2019

(87) PCT Pub. No.: WO2018/221271
PCT Pub. Date: Dec. 6, 2018

(65) Prior Publication Data
US 2020/0110084 A1    Apr. 9, 2020

(30) Foreign Application Priority Data
May 29, 2017  (JP) ................................. 2017-105588

(51) Int. Cl.
*G01N 33/543*    (2006.01)
(52) U.S. Cl.
CPC ............................. *G01N 33/54366* (2013.01)

(58) Field of Classification Search
CPC ........... G01N 33/54366; G01N 33/582; G01N 33/53; G01N 33/531; G01N 33/543
See application file for complete search history.

(56) References Cited

U.S. PATENT DOCUMENTS

| | | | |
|---|---|---|---|
| 2009/0191222 A1 | 7/2009 | Lozupone et al. | |
| 2015/0017660 A1 | 1/2015 | Ochiya | |
| | (Continued) | | |

FOREIGN PATENT DOCUMENTS

| | | | |
|---|---|---|---|
| JP | 2011-510309 A | 3/2011 | |
| JP | 2014-219384 A | 11/2014 | |
| | (Continued) | | |

OTHER PUBLICATIONS

Horikawa et al. (Angew. Chem. Int. Ed. 2016, vol. 55, pp. 13023-13027, online published Sep. 26, 2016) (Year: 2016).*

(Continued)

*Primary Examiner* — Shafiqul Haq
*Assistant Examiner* — Nam P Nguyen
(74) *Attorney, Agent, or Firm* — Knobbe, Martens, Olson & Bear, LLP

(57) ABSTRACT

Provided is a convenient measurement system by which a target to be detected can be quickly recognized with high specificity. This base material for manufacturing a sensor for analyzing a detection target has: a base material; and a polymer film provided on the surface of the base material, wherein the polymer film has a concave that receives the detection target, and the concave has an antibody material bonding group and a signal material bonding group. A sensor for analyzing a detection target has: the base material for manufacturing a sensor for analyzing a detection target; an antibody material specific to the detection target and bonded to the antibody material bonding group; and a signal material that is bonded to the signal material bonding group.

9 Claims, 9 Drawing Sheets

(56) References Cited

U.S. PATENT DOCUMENTS

| | | | |
|---|---|---|---|
| 2016/0033486 A1 | 2/2016 | Itonaga et al. | |
| 2016/0169876 A1 | 6/2016 | Ichiki et al. | |
| 2016/0230235 A1 | 8/2016 | Ichiki et al. | |
| 2016/0334398 A1 | 11/2016 | Weissleder et al. | |
| 2017/0307635 A1 | 10/2017 | Fais et al. | |
| 2021/0333272 A1* | 10/2021 | Takeuchi | G01N 33/54386 |
| 2021/0388139 A1* | 12/2021 | Takeuchi | C08F 8/00 |

FOREIGN PATENT DOCUMENTS

| | | |
|---|---|---|
| JP | 2016-197041 A | 11/2016 |
| JP | 2017-19992 A | 1/2017 |
| WO | WO 2005/056613 A2 | 6/2005 |
| WO | WO 2013/094307 A1 | 6/2013 |
| WO | WO 2015/029979 A1 | 3/2015 |
| WO | WO 2015/045666 A1 | 4/2015 |

OTHER PUBLICATIONS

Hirobumi et al. (Chem. Commun., vol. 50, pp. 1347-1349, published 2014) (Year: 2014).*

Bradley et al. (J. Am. Chem. Soc., vol. 123, pp. 2072-2073, published 2001) (Year: 2001).*

Kempe et al. (Journal of Molecular Recognition, vol. 8, pp. 35-39, published 1995) (Year: 1995).*

Takeuchi et al. ("Dopamine selective molecularly imprinted polymers via post-imprinting modification", Org. Biomol. Chem., vol. 4, pp. 565-568, published 2006). (Year: 2006).*

Kausaite-Minkstimiene, Comparative Study of Random and Oriented Antibody Immobilization Techniques on the Binding Capacity of Immunosensor, Anal. Chem., 2010, vol. 82, pp. 6401-6408. (Year: 2010).*

Vashist et al., Effect of antibody immobilization strategies on the analytical performance of a surface plasmon resonance-based immunoassay, Analyst, vol. 136, pp. 4431-4436, published Sep. 8, 2011. (Year: 2011).*

English Translation of International Search Report in PCT/JP2018/019292, Aug. 21, 2018.

Rupert, Déborah L. M., et al., 2014 "Determination of Exosome Concentration in Solution Using Surface Plasmon Resonance Spectroscopy", Anal. Chem. 86: 5929-5936.

Extended European Search Report in European Patent Application No. 18809084.9 issued Feb. 5, 2021.

Sunayama, H., et al., "Fluorescent protein recognition polymer thin films capable of selective signal transduction of target binding events prepared by molecular imprinting with a post-imprinting treatment," Biosensors and Bioelectronics, vol. 26, No. 2 (Oct. 15, 2010), pp. 458-462.

Horikawa, Ryo, et al., "A Programmable Signaling Molecular Recognition Nanocavity Prepared by Molecular Imprinting and Post-Imprinting Modifications," Angewandte Chemie, vol. 128, No. 42 (Oct. 6, 2016), pp. 13217-13221.

* cited by examiner

BASE MATERIAL FOR MANUFACTURING SENSOR FOR ANALYZING DETECTION TARGET, SENSOR FOR ANALYZING DETECTION TARGET, METHOD FOR ANALYZING DETECTION TARGET

TECHNICAL FIELD

The present invention relates to a technique for quickly detecting a detection target on a base material. More specifically, the present invention relates to a base material for producing a sensor for analysis of a detection target and a manufacturing method thereof, a sensor for analysis of a detection target and a manufacturing method thereof, and a method for analyzing a detection target.

BACKGROUND ART

An exosome is one of vesicles released from a cell, and is a lipid bilayer membrane vesicle having a diameter of 20 to 150 nm. The exosome contains a protein and nucleic acids such as miRNA and mRNA in its inside and also has a protein on its surface. Because the exosome is characterized by such substances, it is thought that by analyzing the characteristics of the exosome, it is possible to presume what the cell that secreted the exosome is. The exosome has been confirmed to be present in various body fluids and can be collected relatively easily.

An exosome secreted from a cancer cell contains a tumor-derived substance. Thus, it is expected that diagnosis of cancer can be performed by analyzing substances contained in the exosome in a body fluid. Further, because an exosome is actively secreted by a cell, it is expected that the exosome exhibits some characteristics even at an early stage of cancer.

Various methods for detecting an exosome have been reported. For example, Patent Document 1 discloses a method of capturing an exosome with a base plate surface-modified with an anchoring substance called BAM (Biocompatible anchor for membrane) and detecting the exosome using an antibody to an antigen molecule on the exosome. Patent Document 2 discloses a method of, in a fluid device including an exosome purification part, a biomolecule purification part, and a biomolecule detection part that are connected each other through a flow path, capturing and fracturing of an exosome at the exosome purification part modified with BAM, and purifying and detecting biomolecules inside the exosome at the biomolecule purification part and the biomolecule detection part, respectively. Patent Document 3 discloses a method of capturing an exosome with a 96-well plate having an immobilized capturing antibody to a surface antigen of the exosome, then adding a detection antibody to another surface antigen, and further adding an enzyme-labeled secondary antibody to the detection antibody to detect the exosome. Patent Document 4 discloses a method of, in a device having a concave in which an antibody to a surface antigen of an exosome is immobilized, capturing the exosome in the concave, then adding a bead on which an antibody to another surface antigen of the exosome is bound, and then counting the bead to detect the exosome. Patent Document 5 discloses a method of, using two types of antibodies of an antibody to a surface antigen of an exosome that is capable of binding to an excitation label and an antibody to another surface antigen of the exosome to which a signal generating label is bound, generating excitation light by energy transfer to detect the exosome when they bind to the exosome and are close each other in the presence of the excitation label. Patent Document 6 discloses a method of detecting an exosome by surface plasmon resonance, using a nanoplasmon sensor including a transparent planar base plate provided with a metal film having nano openings of a predetermined pattern on the surface to generate a detection region that generates surface plasmon resonance during illumination, and an exosome marker-specific capture agent provided on the metal film. Non-Patent Document 1 discloses a method of binding avidin to which an antibody to CD63, a surface antigen of an exosome, is bound to a biotinylated self-assembled monolayer provided on a gold base plate, and measuring the exosome bound via CD63 by surface plasmon resonance.

PRIOR ART DOCUMENTS

Patent Documents

Patent Document 1: International Publication No. 2015/029979
Patent Document 2: International Publication No. 2015/045666
Patent Document 3: Japanese Translation of PCT International Application Publication No. 2011-510309
Patent Document 4: Japanese Patent Laid-open Publication No. 2014-219384
Patent Document 5: International Publication No. 2013/094307
Patent Document 6: US Patent Application Publication No. 2016/0334398

Non-Patent Document

Non-Patent Document 1: Anal. Chem. (2014) 86, 5929-5936

SUMMARY OF THE INVENTION

Problems to be Solved by the Invention

An exosome has been reported to play an important role as an intercellular communication tool that is deeply involved in immune regulation, development of neurodegenerative diseases, organ-specific metastasis of cancer and the like. Thus, achieving to quickly detect the exosome secreted from a cell and to grasp specifically what the detected object is by a simple method is important in detecting intercellular communication tools.

However, in the exosome detection method disclosed in Patent Document 1, after capturing the exosome, an additional step of binding the antibody is necessary, resulting in an inevitable time lag, and thus quick detection is impossible. In the exosome detection method disclosed in Patent Document 2, a complicated system is necessary, in which the internal molecule generated by fracturing the exosome is purified and then the exosome is detected using a substance specific to the internal molecule, making the method complicated. The exosome detection method disclosed in Patent Document 3 is a method of detecting an exosome by sandwich ELISA, thus after capturing the exosome, an additional step of binding the antibody is necessary, resulting in an inevitable time lag, and thus quick detection is impossible. Also, in the exosome detection method disclosed in Patent Document 4, after capturing the exosome, an additional step of binding the antibody beads is necessary, resulting in an inevitable time lag, and thus quick detection is impossible as well. In the exosome detection method disclosed in Patent Document 5, Fluorescence Resonance Energy Transfer is used, thus a complicatedly designed combination of antibodies is necessary, making the method complicated. In the exosome detection methods disclosed in Patent Document 6 and Non-Patent Document 1, surface plasmon resonance that detects the state of a metal surface is used, thus objects nonspecifically adsorbed on the surface are also inevitably detected, and the method lacks the specificity of detecting only the object specifically recognized.

Thus, in view of the above problems, an object of the present invention is to provide a simple measurement system that allows quickly and highly specifically grasping a target to be detected.

Means for Solving the Problem

As a result of intensive studies, the present inventors have found that the above-mentioned object of the present invention can be achieved by configuring a base material so that a polymer film including a concave that receives a detection target will be formed on the surface, an antibody that ensures the binding specificity to the detection target will be placed inside the concave, and a signal substance will be placed only inside the concave. The present invention has been completed through further studies based on this finding.

The present invention includes a base material for producing a sensor for analysis of a detection target and a manufacturing method thereof, a sensor for analysis of a detection target and a manufacturing method thereof, and a method for analyzing a detection target. That is, the present invention provides the invention having the aspects described below.

Item 1. A base material for producing a sensor for analysis of a detection target, including:
  a base material; and
  a polymer film provided on a surface of the base material, wherein the polymer film includes a concave that receives the detection target, and inside the concave, a group for binding antibody substance and a group for binding signal substance.

Item 2. The base material for producing a sensor for analysis of a detection target according to item 1, wherein the polymer film is composed of a molecularly imprinted polymer produced using the detection target or an object larger in size than the detection target as a template, and the concave corresponds to a part of a surface shape of the template.

Item 3. The base material for producing a sensor for analysis of a detection target according to item 1 or 2, wherein the group for binding antibody substance is a chelate-forming binding group.

Item 4. The base material for producing a sensor for analysis of a detection target according to any one of items 1 to 3, wherein the group for binding signal substance is a thiol group.

Item 5. A sensor for analysis of a detection target, including:
  the base material for producing a sensor for analysis of a detection target according to any one of items 1 to 4;
  an antibody substance specific to the detection target that is bound to the group for binding antibody substance; and
  a signal substance that is bound to the group for binding signal substance.

Item 6. The sensor for analysis of a detection target according to item 5, wherein the detection target is a microparticle having a membrane structure.

Item 7. The sensor for analysis of a detection target according to item 6, wherein the microparticle having a membrane structure is an exosome.

Item 8. The sensor for analysis of a detection target according to any one of items 5 to 7, wherein the antibody substance specific to the detection target has a specific bindability to a specific antigen expressed on a surface of the microparticle having a membrane structure.

Item 9. A method for analyzing a detection target, including:
  a step of contacting a sample containing a detection target with the sensor for analysis of a detection target according to any one of items 5 to 8 to bind the detection target to the antibody substance; and
  a step of detecting a change in signal derived from the signal substance.

Item 10. A manufacturing method of a base material for producing a sensor for analysis of a detection target, including:
  a molecular film-forming step of forming on a base material a molecular film having a binding functional group and a polymerization initiating group on a surface of the molecular film;
  a template introduction step of introducing an artificial particle as a template via a first reversible linked group to the binding functional group;
  a surface modification step of modifying a surface of the template with a polymerizable functional group via a second reversible linked group;
  a polymerization step of forming a polymer film on a surface of the base material by adding a polymerizable monomer and synthesizing a molecularly imprinted polymer corresponding to a part of the surface of the template using the polymerizable monomer as a substrate and the polymerization initiating group as a polymerization initiator; and
  a removal step of cleaving the first reversible linked group and the second reversible linked group to convert the first reversible linked group and the second reversible linked group into a group for binding antibody substance and a group for binding signal substance, respectively, and removing the template.

Item 11. The manufacturing method of a base material for producing a sensor for analysis of a detection target according to item 10, wherein the artificial particle includes on a surface of the artificial particle a group capable of forming the first reversible linked group by binding to the group for binding antibody substance and a reversible bond group capable of forming the second reversible linked group by binding to the group for binding signal substance.

Item 12. The manufacturing method of a base material for producing a sensor for analysis of a detection target according to item 10 or 11, wherein the artificial particle is a silica particle.

Item 13. The manufacturing method of a base material for producing a sensor for analysis of a detection target according to any one of items 10 to 12, wherein the group for binding antibody substance is a chelate-forming binding group, and the group capable of forming the first reversible linked group by binding to the group for binding antibody substance is a histidine tag.

Item 14. The manufacturing method of a base material for producing a sensor for analysis of a detection target according to any one of items 10 to 13, wherein the group for binding signal substance is a thiol group, and the reversible bond group capable of forming the second reversible linked group by binding to the group for binding signal substance is a thiol group.

Item 15. A manufacturing method of a sensor for analysis of a detection target, including:
- a step of performing the manufacturing method of a base material for producing a sensor for analysis of a detection target according to any one of items 10 to 14;
- a step of binding an antibody substance specific to the detection target to the group for binding antibody substance; and
- a step of binding a signal substance to the group for binding signal substance.

Advantages of the Invention

According to the present invention, a simple measurement system that allows to quickly and highly specifically grasp a target to be detected is provided.

EMBODIMENTS OF THE INVENTION

[1. Base Material for Producing Sensor for Analysis of Detection Target]

The base material for producing a sensor for analysis of a detection target of the present invention is a base material that is a material for producing the sensor for analysis of the invention below. This base material for producing a sensor for analysis is configured so that a user can easily customize the base material into a sensor capable of quickly detecting a detection target such as an exosome.

Figure 1:
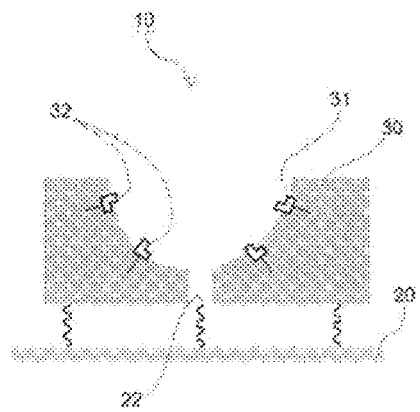
FIG. 1 shows a schematic diagram showing one example of a base material for producing a sensor for analysis of a detection target of the present invention.

The base material for producing a sensor for analysis of a detection target of the present invention includes: a base material; and a polymer film provided on a surface of the base material, wherein the polymer film includes a concave that receives a detection target, and inside the concave, a group for binding antibody substance and a group for binding signal substance. One example of the base material for producing a sensor for analysis of a detection target of the present invention is schematically shown in FIG. 1. As shown in FIG. 1, a base material for producing a sensor for analysis 10 includes a base material 20 and a polymer film 30. The polymer film 30 is provided on the surface of the base material 20 and includes a concave 31. The concave 31 is a hole formed in a size capable of receiving a detection target (a detection target 60 below). The base material for producing a sensor for analysis 10 includes a group for binding antibody substance 22 and a group for binding signal substance 32 inside the concave 31. The group for binding signal substance 32 is provided in the vicinity of the group for binding antibody substance 22. Each element will be described in detail below.

[1-1. Base Material]

The material of the base material 20 can be a material selected from the group consisting of, for example, metal, glass, and resin. Examples of the metal include gold, silver, copper, aluminum, tungsten, and molybdenum. Examples of the resin include poly (meth)acrylate, polystyrene, ABS (acrylonitrile-butadiene-styrene copolymer), polycarbonate, polyester, polyethylene, polypropylene, nylon, polyurethane, silicone resin, fluororesin, methylpentene resin, phenol resin, melamine resin, epoxy resin, and vinyl chloride resin.

The base material 20 can be formed by combining multiple materials selected from the materials above. For example, the base material 20 can be a base material provided with a metal film on the surface of glass or resin. The shape of the base material 20 can be a plate shape or a particle shape. Preferred examples include a gold base plate, a glass base plate, a gold nanoparticle, and a glass bead.

[1-2. Polymer Film]

The polymer film 30 is layered on the base material 20 and includes multiple concaves 31. The concave 31 is a sensing place in the sensor for analysis of a detection target of the present invention. The concave 31 is not limited as long as it is formed so that a detection target can be received. For example, the concave 31 can be a molecularly imprinted polymer (MIP) formed using molecularly imprinting polymerization as described below. In this case, the concave 31 is formed by a template (a template 40 below) used in molecular imprinting polymerization, and has a shape corresponding to a part of the surface shape of the template. The concave 31 only needs to be formed in a size capable of receiving a detection target, and thus the template of the concave 31 can be the same as the detection target or an object larger in size than the detection target. "The concave 31 is formed in a size capable of receiving a detection target" means that the size of the concave 31 on the surface of the base material 20 is sufficient to allow at least a part of a detection target to enter inside the concave 31 and approach to an antibody substance to bind it when the antibody substance (an antibody substance 52 below) and a signal substance (a signal substance 53 below) are bound to form a sensor for analysis (a sensor for analysis 50 below). The opening diameter of the concave 31 can vary depending on the detection target, thus it is not particularly limited, and it can be, for example, 1 nm to 10 μm. The thickness of the polymer film 30 can also vary depending on the detection target, thus it is not particularly limited, and it can be, for example, 1 nm to 1 μm.

The polymer that constitutes the polymer film 30 can be, for example, a biocompatible polymer containing a component derived from a biocompatible monomer. Biocompatibility refers to a property of not inducing the adhesion of biological substances. By containing a component derived from a biocompatible monomer, nonspecific adsorption can be favorably inhibited in the polymer film 30. The biocompatible monomer is preferably a hydrophilic monomer, more preferably a zwitterionic monomer.

A zwitterionic monomer contains both an anionic group derived from an acidic functional group (for example, a phosphoric acid group, a sulfuric acid group, and a carboxyl group) and a cationic group derived from a basic functional group (for example, a primary amino group, a secondary amino group, a tertiary amino group, and a quaternary ammonium group) in one molecule. Examples thereof include phosphobetaine, sulfobetaine, and carboxybetaine.

More specifically, examples of the phosphobetaine include a molecule having a phosphorylcholine group in the side chain, and preferably include 2-methacryloyloxyethyl phosphorylcholine (MPC).

Examples of the sulfobetaine include N,N-dimethyl-N-(3-sulfopropyl)-3'-methacryloylaminopropaneaminium inner salt (SPB) and N,N-dimethyl-N-(4-sulfobutyl)-3'-methacryloylaminopropaneaminium inner salt (SBB).

Examples of the carboxybetaine include N,N-dimethyl-N-(1-carboxymethyl)-2'-methacryloyloxyethaneaminium inner salt (CMB) and N,N-dimethyl-N-(2-carboxyethyl)-2'-methacryloyloxyethaneaminium inner salt (CEB).

The percentage of the component derived from a biocompatible monomer in the polymer film 30 can be, for example, 5 mol % or more and 100 mol % or less. The content of the component derived from a biocompatible monomer of the above-mentioned lower limit or more is preferred in terms of inhibiting non-specific adsorption on the surface of the polymer film 30. The percentage of the component derived from a biocompatible monomer in the polymer film 30 can be preferably 10 mol % or more and 80 mol % or less, further preferably 20 mol % or more and 60 mol % or less.

[1-3. Group for Binding Antibody Substance]

The group for binding antibody substance 22 is a group that allows an antibody substance to be introduced into the base material for producing a sensor for analysis 10 by directly or indirectly binding the antibody substance (an antibody substance 52 below). The user can freely target a detection target, freely select the antibody substance specific to the detection target to be targeted, and introduce it to the group for binding antibody substance 22. By introducing one type of antibody substances into one concave 31, and introducing another type of antibody substances into another concave 31 in one base material 20, customization can be made so that the analysis of the detection target using multiple types of antibody substances will be achieved in one base material 20. As a specific example of such customization, both an exosome and a protein can be analyzed in one base material 20 by introducing an antibody substance that binds to an exosome into one concave 31 and introducing an antibody substance that binds to a protein into another concave 31.

In the present invention, at least one group for binding antibody substance 22 needs to be provided in one concave 31, and multiple groups for binding antibody substance 22 can be provided in one concave 31. The group for binding antibody substance 22 is not provided on the part other than the concave 31 on the surface of the base material 20.

The group for binding antibody substance 22 can be an irreversible binding group, a reversible binding group, a covalent binding group, or a non-covalent binding group. The group for binding antibody substance 22 is preferably a reversible binding group, more preferably a non-covalent binding group. Examples of such a group include a chelate-forming binding group. The chelate-forming binding group is capable of indirectly binding an antibody substance via a substance that binds to the Fc region of the antibody substance such as Protein G.

The chelate-forming binding group is not particularly limited as long as it is a group that has a ligand having multiple coordination positions (a multidentate ligand) and binds (coordinates) to a metal ion. Examples thereof include an amino polycarboxylic acid chelating agent-derived group, a hydroxycarboxylic acid chelating agent-derived group, a deferoxamine-derived group, a deferasirox-derived group, a deferiprone-derived group, and a histidine tag, and preferably include an amino polycarboxylic acid chelating agent-derived group.

Examples of the amino polycarboxylic acid include ethylenediaminetetraacetic acid (EDTA), ethylenediaminediacetic acid, hydroxyethylethylenediaminetriacetic acid (HEDTA), dihydroxyethylethylenediaminetetraacetic acid (DHEDDA), nitrilotriacetic acid (NTA), hydroxyethyliminodiacetic acid (HIDA), N-(2-hydroxyethyl) iminodiacetic acid, β-alanine diacetic acid, cyclohexanediaminetetraacetic acid, iminodiacetic acid, N-(2-hydroxyethyl) iminodiacetic acid, diethylenetriaminepentaacetic acid (DTPA), N-(2-hydroxyethyl) ethylenediaminetriacetic acid, glycol ether diamine tetraacetic acid, glutamic acid diacetic acid, aspartic acid diacetic acid, methylglycine diacetic acid, iminodisuccinic acid, serine diacetic acid, hydroxyiminodisuccinic acid, dihydroxyethylglycine, aspartic acid, glutamic acid, and triethylenetetramine-N,N,N',N'',N''',N'''-hexaacetic acid, and preferably include nitrilotriacetic acid (NTA).

The reversible binding group is a group capable of constituting a reversible linked group by binding to other reversible binding group (covalently or non-covalently), and reversible means that both conversion of a reversible binding group into a reversible linked group (bond) and conversion of a reversible linked group into a reversible binding group (cleavage) are bidirectionally possible (the same applies hereinafter).

[1-4. Group for Binding Signal Substance]

The group for binding signal substance 32 is a group that allows a signal substance to be introduced into the base material for producing a sensor for analysis 10 by binding the signal substance (a signal substance 53 below). The user can freely select the signal substance and introduce it into the group for binding signal substance 32. When one concave 31 and other concave 31 have different types of antibody substances provided thereon in one base material 20, customization can be made so that different signal substances are provided depending on the type of antibody substances.

In the present invention, multiple groups for binding signal substance 32 are usually provided for one concave 31. The group for binding signal substance 32 only needs to be provided in sufficient amount to detect the signal intensity change when sensing is performed in the concave 31 of the analysis sensor of the present invention (when the detection target is received in the concave 31). Thus, the amount of the group for binding signal substance 32 to be provided in one concave 31 is not particularly limited, and it can be, for example, about 100 to about 1000 per concave 31 depending on the size of the concave 31 and the size of the target substance to be detected. The group for binding signal substance 32 is not provided on the part other than the concave 31 on the surface of the base material 20.

The group for binding signal substance 32 can be an irreversible binding group, a reversible binding group, a covalent binding group, or a non-covalent binding group. The group for binding signal substance 32 is preferably a reversible binding group, more preferably a covalent binding group. Examples of such a group include a thiol group (the corresponding reversible linked group is a disulfide group), an aminooxy group or a carbonyl group (the corresponding reversible linked group is an oxime group), a boronic acid group and a diol group (the corresponding reversible linked group is a cyclic diester group), an amino group and a carbonyl group (the corresponding reversible linked group is a Schiff base), and an aldehyde group or ketone group and alcohol (the corresponding reversible linked group is an acetal group).

[1-5. Other Aspects]

The base material for producing a sensor for analysis of a detection target of the present invention only needs to be configured so that at least one of the antibody substance and the signal substance can be customized by the user. Thus, in another aspect, it is possible that an antibody substance specific to the detection target has already been bound to the group for binding antibody substance. In this case, the user can freely select and introduce the signal substance.

In yet another aspect, it is possible that the signal substance has already been bound to the group for binding signal substance. In this case, the user can freely target a detection target, and freely select and introduce the antibody substance specific to the detection target to be targeted.

[2. Sensor for Analysis of Detection Target]

Figure 2:
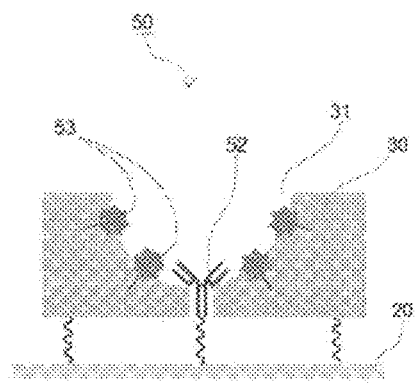
FIG. 2 shows a schematic diagram showing one example of a sensor for analysis of a detection target of the present invention.

The sensor for analysis of a detection target of the present invention includes: the base material for producing a sensor for analysis of a detection target; an antibody substance specific to the detection target that is bound to the group for binding antibody substance; and a signal substance that is bound to the group for binding signal substance. One example of a sensor for analysis of a detection target of the present invention is schematically shown in FIG. 2. As shown in FIG. 2, in the sensor for analysis 50, an antibody substance 52 is bound to the group for binding antibody substance 22, and a signal substance 53 is bound to the group for binding signal substance 32 in the base material for producing a sensor for analysis 10 above.

[2-1. Detection Target]

The detection target (the detection target 60 below) of the sensor for analysis of the present invention is not particularly limited in principle as long as it has specific bindability to the antibody substance 52. Specific examples thereof include a low molecular weight substance, a protein, and a microparticle having a membrane structure. Examples of the low molecular weight substance include any substances such as a hormone, an agent, a herbicide, an agricultural chemical, sugar, cholesterol, a lipid, uric acid, an environmental hormone, and a peptide. Examples of the protein include any proteins such as HSA, IgG, fibrinogen, transferrin, AST, ALT, LDH, ALP, LAP, γ-GTP, CRP, AFP, and PSA. Examples of the microparticle having a membrane structure include an extracellular microparticle, an intracellular vesicle, an organelles, and a cell. Examples of the membrane structure include a lipid bilayer membrane structure. Examples of the extracellular microparticle include an exosome, a microvesicle, and an apoptotic body. Examples of the intracellular vesicle include a lysosome and an endosome. Examples of the organelle include a mitochondrion. Examples of the cell include a cancer cell such as a circulating tumor cell (CTC) and other disease-related cells.

As described later, when the signal substance 53 is configured as one of the fluorescent dye pair that causes fluorescence resonance energy transfer (FRET), the detection target 60 is bound to the other of the fluorescent dye pair in advance.

[2-2. Antibody Substance (Antibody Substance Specific to Detection Target)]

The antibody substance 52 only needs to have a specific bindability to the detection target. The antibody substance 52 is intended to include an antibody and an antibody-like substance. The antibody refers to a protein having a complete basic structure of an immunoglobulin, and the antibody-like substance refers to a fragment of an immunoglobulin (an antibody fragment). Examples of the antibody include an immunoglobulin (Ig) and a chimeric antibody, and more specifically include IgG, IgA, IgM, IgE, and IgD. Examples of the chimeric antibody include a humanized antibody. The antibody can be derived from mammals such as a mouse, a rabbit, a cow, a pig, a horse, a sheep, and a goat, birds such as a chicken, and animal species such as a human, and is not particularly limited. The antibody can be prepared, for example, from a serum derived from the above-mentioned animal species by a conventionally known method, or a commercially available antibody can be used. The antibody can be, for example, a polyclonal antibody or a monoclonal antibody, and is preferably a monoclonal antibody. Examples of the antibody-like substance include Fab, Fab', F(ab')$_2$, and ScFv.

The antibody substance 52 can be appropriately selected by those skilled in the art according to the detection target. When the detection target has a specific antigen on its surface, one having specific bindability to the specific antigen can be used as the antibody substance 52. For example, when the detection target is an exosome, because the exosome has, for example, CD63, CD9, CD81, CD37, CD53, CD82, CD13, CD11, CD86, ICAM-1, Rab5, Annexin V, LAMP1 or the like as a membrane protein (an exosome-specific antigen), an antibody to the exosome-specific antigen can be used as the antibody substance 52. When the detection target is a cancer cell, because the cancer cell has, for example, Caveolin-1, EpCAM, FasL, TRAIL, Galectine3, CD151, Tetraspanin 8, EGFR, HER2, RPN2, CD44, TGF-β or the like as a cancer cell-specific antigen, an antibody to the cancer cell-specific antigen can be used as the antibody substance 52. Similarly, when the detection target is a disease cell other than the above, an antibody to the disease cell-specific antigen can be used as the antibody substance 52.

As the antibody substance 52, one having no modifying group can be used from the viewpoint of convenience and good affinity of the antibody substance to the detection target, and from the viewpoint of ease of production or versatility of the sensor for analysis 50. The modifying group in this case refers to a modifying group provided for a purpose other than affinity, such as the signal substance. Meanwhile, the modifying group does not include a group that contributes to the binding to the group for binding antibody substance 22 (for example, a histidine tag).

[2-3. Signal Substance]

The signal substance 53 functions as a reader of the information for binding between an antibody substance specific to the detection target 52 and the group for binding antibody substance 22. The signal substance 53 is not particularly limited as long as the detected signal intensity is changed or spectrum is changed (for example, the peak is shifted) by the binding of the detection target to the concave 31. Examples thereof include a fluorescent substance, a radioactive element-containing substance, and a magnetic substance. From the viewpoint of ease of detection and the like, the signal substance is preferably a fluorescent substance. Examples of the fluorescent substance include a fluorescein dye, a cyanine dye such as an indocyanine dye, a fluorescent dye such as rhodamine dyes, a fluorescent protein such as GFP, and a nanoparticle such as colloidal gold and a quantum dot. Examples of the radioactive element-containing substance include sugar, an amino acid, and a nucleic acid labeled with a radioactive isotope such as $^{18}$F. Examples of the magnetic substance include those having a magnetic body such as ferrichrome, and those found in a ferrite nanoparticle and a nanomagnetic particle.

The signal substance 53 can be configured as one of fluorescent dye pair that causes fluorescence resonance energy transfer (FRET). The fluorescent dye pair that causes FRET is not particularly limited, and a donor dye or an acceptor dye can be selected as the signal substance 53 without limitation. Preferably, a donor dye can be selected as the signal substance 53. Specific examples of donor/acceptor dyes that constitute the fluorescent dye pair that causes FRET include fluorescein isothiocyanate (FITC)/tetramethylrhodamine isothiocyanate (TRITC), Alexa Fluor647/Cy5.5, HiLyte Fluor647/Cy5.5, and R-phycoerythrin (R-PE)/allophycocyanin (APC).

[3. Manufacturing Method of Base Material for Producing Sensor for Analysis of Detection Target]

The manufacturing method of a base material for producing a sensor for analysis of a detection target of the present invention includes the following steps.

A molecular film-forming step of forming on a base material a molecular film having a binding functional group and a polymerization initiating group on a surface of the molecular film;

a template introduction step of introducing a template via a first reversible linked group to the binding functional group;

a polymerization step of forming a polymer film on a surface of the base material by adding a polymerizable monomer and synthesizing a molecularly imprinted polymer corresponding to a part of the surface of the template using the polymerizable monomer as a substrate and the polymerization initiating group as a polymerization initiator; and a removal step of removing the template.

[3-1. When Exosome is Used as Template]

An exosome can be used as a template. The manufacturing method of the base material for producing a sensor for analysis of a detection target of the present invention when an exosome is used as a template is schematically shown in FIGS. 3 to 7. The manufacturing method of the base material for producing a sensor for analysis of a detection target in this case includes the following steps.

Figure 3:
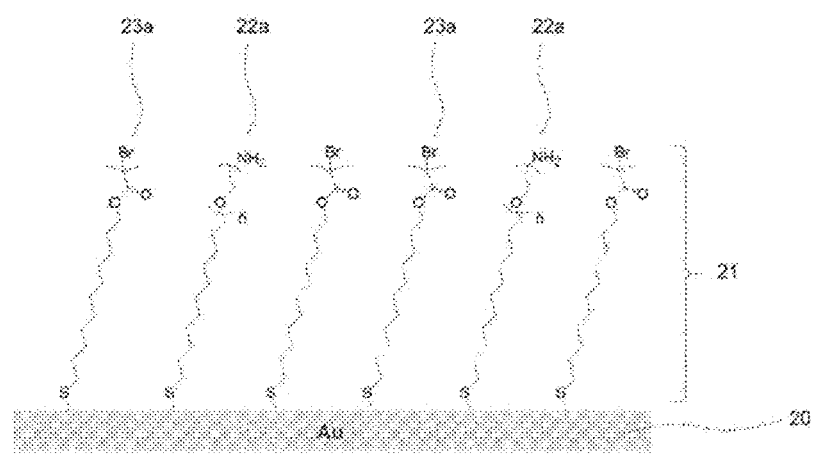
FIG. 3 shows a schematic diagram describing a molecular film-forming step in the manufacturing method of a base material for producing a sensor for analysis of a detection target of the present invention.
Figure 4:
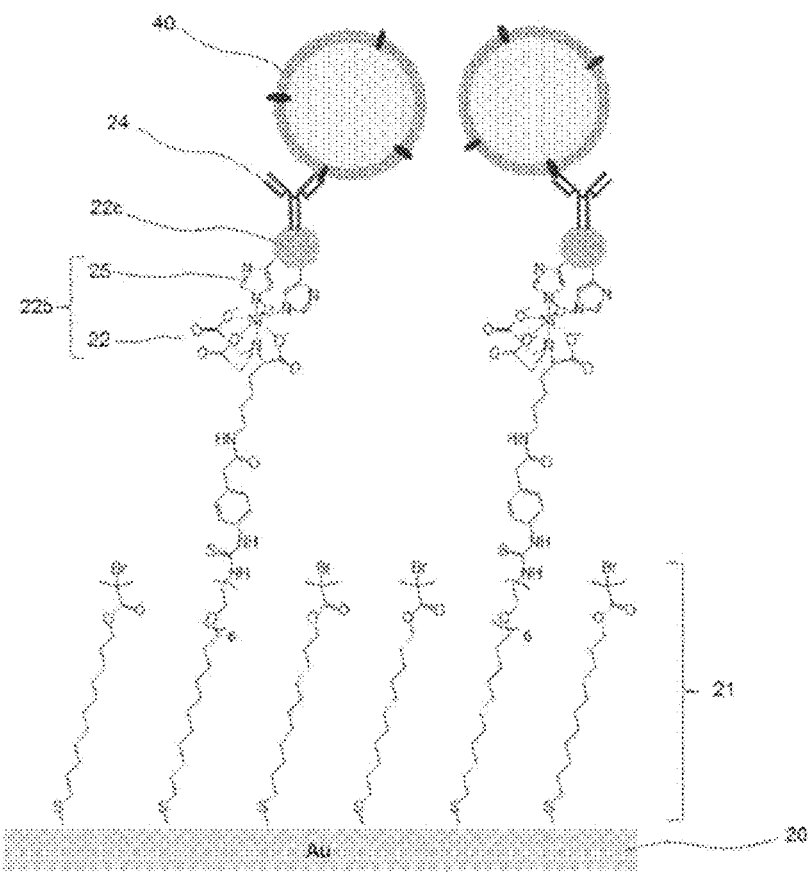
FIG. 4 shows a schematic diagram describing a template introduction step subsequent to FIG. 3 (when an exosome is used as a template).
Figure 5:
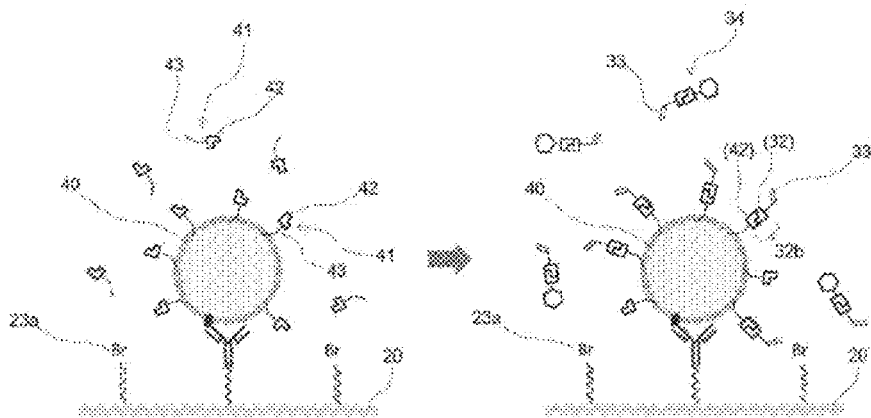
FIG. 5 shows a schematic diagram describing a surface modification step subsequent to FIG. 4 (when an exosome is used as a template).
Figure 6:
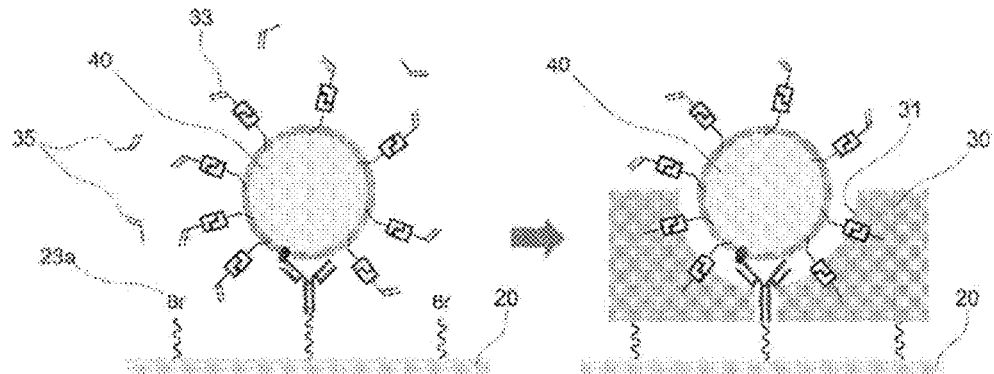
FIG. 6 shows a schematic diagram describing a polymerization step subsequent to FIG. 5 (when an exosome is used as a template).
Figure 7:
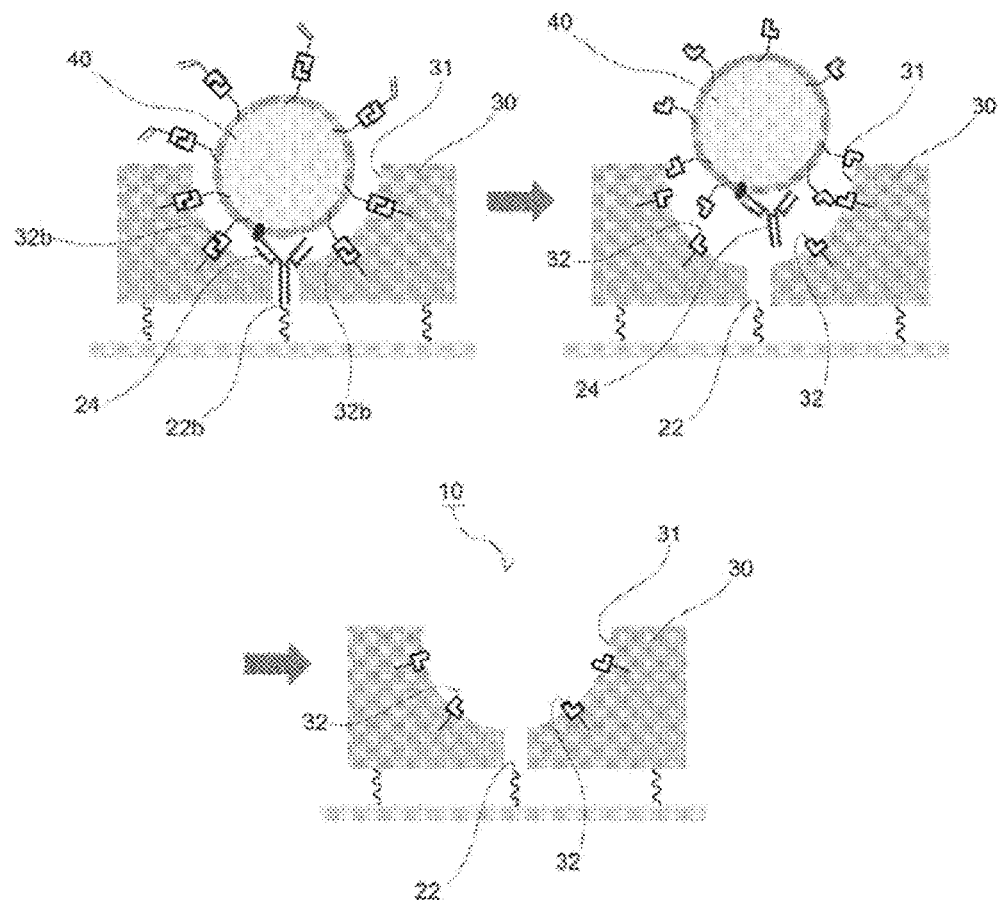
FIG. 7 shows a schematic diagram describing a removal step subsequent to FIG. 6 (when an exosome is used as a template).

A molecular film-forming step of forming on a base material 20 a molecular film 21 having a binding functional group 22a and a polymerization initiating group 23a on a surface of the molecular film (FIG. 3);

a template introduction step of introducing a template 40 that specifically binds to an antibody substance 24 via a first reversible linked group 22b and the antibody substance 24 to the binding functional group 22a (FIG. 4);

a surface modification step of modifying a surface of the template 40 with a polymerizable functional group 33 via a second reversible linked group 32b (FIG. 5);

a polymerization step of forming a polymer film 30 on a surface of the base material 20 by adding a polymerizable monomer 35 and synthesizing a molecularly imprinted polymer corresponding to a part of the surface of the template 40 using the polymerizable functional group 33 and the polymerizable monomer 35 as a substrate and the polymerization initiating group 23a as a polymerization initiator (FIG. 6); and a removal step of cleaving the first reversible linked group 22b and the second reversible linked group 32b to convert the first reversible linked group 22b and the second reversible linked group 32b into a group for binding antibody substance 22 and a group for binding signal substance 32, respectively, and removing the antibody substance 24 and the template 40 (FIG. 7).

Each step will be described in detail below with reference to the drawings.

[3-1-1. Molecular Film-Forming Step]

As shown in FIG. 3, in the molecular film-forming step, a molecular film 21 having a binding functional group 22a and a polymerization initiating group 23a on the surface is formed on a base material 20.

The binding functional group 22a is a group different from the polymerization initiating group 23a, and a group according to the reagent used for extending the molecular chain to the template 40 in the template introduction step below is appropriately determined by those skilled in the art. In the illustrated aspect, the case where the binding functional group 22a is an amino group is illustrated.

The polymerization initiating group 23a is not particularly limited as long as it has a structure capable of functioning as a polymerization initiator, and it can be appropriately determined by those skilled in the art according to the polymerization reaction used in the polymerization step below. Examples of the polymerization initiating group 23a include a group having a structure that generates a radical during polymerization reaction, specifically, a carbon-halogen binding group derived from an organic halogen (—CX group; X represents a halogen atom). In the illustrated aspect, the case where the polymerization initiating group 23a is a —CBr group is illustrated.

The molecular film 21 can be formed by a conventionally known method as a monolayer formed by mixed self-assembly using a molecule having a binding functional group 22a at the end, and a molecule having a polymerization initiating group 23a at the end. Thus, the molecular film 21 can be formed as a mixed self-assembled monolayer (mixed SAMs).

[3-1-2. Template Introduction Step]

As shown in FIG. 4, in the template introduction step, a template 40 that specifically binds to an antibody substance 24 is introduced via a first reversible linked group 22b and an antibody substance 24 to the binding functional group 22a.

More specifically, the template introduction step can include the following steps.

A step of introducing an antibody substance-binding group 22c via a first reversible linked group 22b to the binding functional group 22a;
  a step of binding an antibody substance 24 to the antibody substance-binding group 22c; and
  a step of binding a template 40 to the antibody substance 24.

The first reversible linked group 22b is not particularly limited as long as it is a group capable of bidirectional conversion from the first reversible linked group 22b into a reversible binding group (that is, the above-mentioned group for binding antibody substance 22) by cleavage and from a reversible binding group (that is, the above-mentioned group for binding antibody substance 22) into the first reversible linked group 22b by binding. Preferably, the first reversible linked group 22b can be a chelate-bound group in which chelate-forming binding groups are bound each other via metal coordination. In the illustrated aspect, as the first reversible linked group 22b, a structure is illustrated in which an NTA group (a type of the group for binding antibody substance 22), which is an amino polycarboxylic acid chelating agent-derived group, and a histidine tag, which is a group 25 capable of forming a first reversible linked group 22b by binding to the group for binding antibody substance 22 (because the histidine tag in the figure is schematically shown, the exact molecular structure is not shown, and the imidazolyl group, a part of the histidine tag, is highlighted), are chelate bound via a nickel ion.

Though the antibody substance-binding group 22c is not particularly limited as long as it is a group capable of binding to the antibody substance 24, it is preferably a group having specific bindability to the Fc region of the antibody substance 24 from the viewpoint of oriented binding of the antibody substance 24 (that is, binding in a direction in which the binding part of the antibody substance 24 to the template 40 faces outward). In the illustrated aspect, Protein G is illustrated as such a group.

The antibody substance 24 can be determined according to the template 40. Specifically, an antibody substance having specific bindability to the template 40 is selected as the antibody substance 24. The template 40 is determined in consideration of the detection target. Specifically, an object that is the same as the detection target (the detection target 60 below) or an object larger in size than the detection target is selected as a template. The object larger in size than the detection target is not particularly limited as long as it has a shape and size that allow the concave 31 formed in the synthesis of the polymer film 30 in the polymerization step below to be a size that is large enough to receive the detection target on the surface of the base material 20, and examples thereof include a biomolecule such as a protein and a microparticle having a membrane structure.

Because the template 40 is bound via the antibody substance 24, a template having on the surface an antigen to which the antibody substance 24 specifically binds is preferably used. For example, an antibody to a specific antigen on the exosome surface (a surface protein) can be used as the antibody substance 24, and an exosome can be used as the template 40.

In the illustrated aspect, as the procedure of the template introduction step, an aspect is illustrated in which a molecule having an NTA group, which is an amino polycarboxylic acid chelating agent-derived group, is bound to the amino group as the binding functional group 22a, Protein G as the antibody substance-binding group 22c is introduced via the first reversible linked group 22b (a chelate group) by reacting recombinant Protein G with a histidine tag in the presence of nickel ions, then further, as an antibody substance 24, an antibody specific to the exosome surface protein is bound, and finally, an exosome as a template 40 is bound.

[3-1-3. Surface Modification Step]

As shown in FIG. 5, in the surface modification step, the surface of the template 40 is modified with a polymerizable functional group 33 via a second reversible linked group 32b.

More specifically, the surface modification step can include the following steps.

Anchoring an anchoring substance 41 including an anchoring group 43 and a reversible binding group 42 to the template 40; and
Converting the reversible binding group 42 into the second reversible linked group 32b and introducing the polymerizable functional group 33.

The anchoring substance 41 is a substance including the anchoring group 43 and the reversible binding group 42. The anchoring group 43 is a group capable of being anchored to the template 40, and in particular, when the template 40 is a membrane body having a lipid bilayer membrane, the anchoring group 43 is preferably a hydrophobic chain group capable of being anchored to the lipid bilayer membrane. The hydrophobic chain can be of a single chain or multiple chains, can be a saturated hydrocarbon or an unsaturated hydrocarbon, and can be a hydrophobic chain with a substituent or a hydrophobic chain without a substituent. Specifically, the hydrophobic chain is preferably a linear or branched alkyl group or alkenyl group having 6 to 24 carbon atoms, and more specific examples thereof include a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, a stearyl group (an octadecyl group), a nonadecyl group, an icosyl group, a heicosyl group, a docosyl group, a tricosyl group, a tetracosyl group, a myristol group, a palmitoleyl group, an oleyl group, a linoyl group, a linoleyl group, a lisinoleyl group, and an isostearyl group. Among these, a myristol group, a palmitoleyl group, an oleyl group, a linoyl group, and a linoleyl group are preferred, and an oleyl group is more preferred.

The anchoring substance 41 can include a hydrophilic chain group in addition to the anchoring group 43 and the reversible binding group 42. The hydrophilic chain group can be a linking group located between the anchoring group 43 and the reversible binding group 42. Specific examples thereof include a protein, an oligopeptide, a polypeptide, polyacrylamide, polyethylene glycol (PEG), and a dextran, and more preferably include PEG.

The reversible binding group 42 can be a group that is converted into a second reversible linked group 32b by binding to other reversible binding group (specifically the above-mentioned group for binding signal substance 32). Examples thereof include a thiol group (the corresponding second reversible linked group 32b is a disulfide group), an aminooxy group or a carbonyl group (the corresponding second reversible linked group 32b is an oxime group), a boronic acid group and a diol group (the corresponding second reversible linked group 32b is a cyclic diester group), an amino group and a carbonyl group (the corresponding second reversible linked group 32b is a Schiff base), and an aldehyde group or ketone group and alcohol (the corresponding second reversible linked group 32b is an acetal group).

Specific examples of the preferred anchoring substance 41 include the substance represented by the following formula (BAM-SH). In the formula, n represents, for example, an integer of 0 to 182.

The polymerizable functional group 33 only needs to have a polymerizable unsaturated bond, and representative examples thereof include a (meth)acryl group.

In the illustrated aspect, as the procedure of the surface modification step, an aspect is illustrated in which by anchoring of the anchoring substance 41 represented by the formula above to the lipid bilayer membrane of the exosome as the template 40, and subsequent disulfide exchange from a molecule including a (meth)acrylic group as a polymerizable functional group 33 and a disulfide bond 34 to the thiol group, a second reversible binding group 42 of the anchoring substance 41, the thiol group is converted into a disulfide group, the second reversible linked group 32b, and the surface of the template 40 is modified with the polymerizable functional group 33.

In this way, in the surface modification step, by introducing the second reversible linked group 32b that is capable of generating the group for binding signal substance 32 by surface modification of the template 40, the second reversible linked group 32b can be delivered only to the surface of the template 40.

[3-1-4. Polymerization Step]

As shown in FIG. 6, in the polymerization step, the polymerizable monomer 35 is added, and a molecularly imprinted polymer corresponding to a part of the surface of the template 40 is synthesized using the polymerizable functional group 33 and the polymerizable monomer 35 as a substrate and the polymerization initiating group 23a as a polymerization initiator. Thus, the polymer film 30 including the concaves 31 is formed on the surface of the base material 20. In this specification, for convenience, a polymer synthesized by imprinting polymerization with a template is described as a molecular imprint polymer, and the molecularly imprinted polymer includes a polymer synthesized by imprinting polymerization with a template other than a molecule (for example, a cell).

The polymerizable monomer 35, as described in the polymer film 30 above, the biocompatible monomer is preferably a hydrophilic monomer, more preferably a zwitterionic monomer.

A zwitterionic monomer contains both an anionic group derived from an acidic functional group (for example, a phosphoric acid group, a sulfuric acid group, and a carboxyl group) and a cationic group derived from a basic functional group (for example, a primary amino group, a secondary amino group, a tertiary amino group, and a quaternary

[Chemical Formula 1]

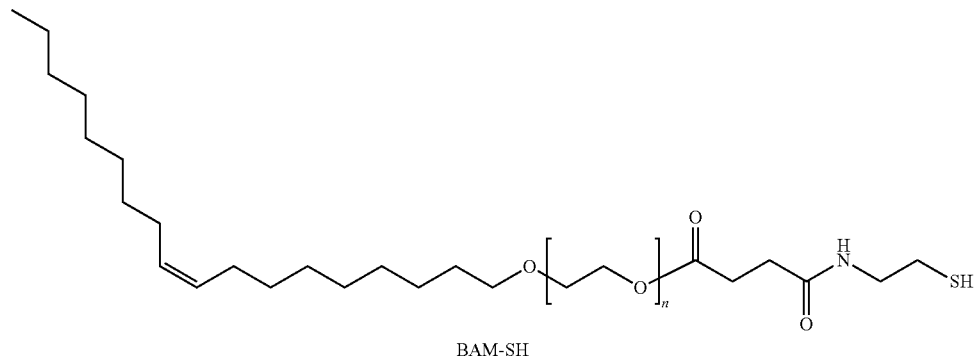

BAM-SH ammonium group) in one molecule. Examples thereof include phosphobetaine, sulfobetaine, and carboxybetaine.

More specifically, examples of the phosphobetaine include a molecule having a phosphorylcholine group in the side chain, and preferably include 2-methacryloyloxyethyl phosphorylcholine (MPC).

The sulfobetaine include N,N-dimethyl-N-(3-sulfopropyl)-3'-methacryloylaminopropaneaminium inner salt (SPB) and N,N-dimethyl-N-(4-sulfobutyl)-3'-methacryloylaminopropaneaminium inner salt (SBB).

Examples of the carboxybetaine include N,N-dimethyl-N-(1-carboxymethyl)-2'-methacryloyloxyethanaminium inner salt (CMB) and N,N-dimethyl-N-(2-carboxyethyl)-2'-methacryloyloxyethaneaminium inner salt (CEB).

Surface-initiated living radical polymerization proceeds by the construction of a polymerization reaction system in which the polymerizable functional group 33, the polymerizable monomer 35, the polymerization initiating group 23a, and the template 40 coexist on the surface of the base material 20. The polymerization reaction system preferably further includes a transition metal complex formed by a transition metal or a transition metal compound and a ligand as a polymerization catalyst, and more preferably a reducing agent is used. Examples of the transition metal or transition metal compound include metal copper or a copper compound, and examples of the copper compound include a chloride, a bromide, an iodide, a cyanide, an oxide, a hydroxide, an acetate, a sulfate, and a nitrate, and preferably include a bromide. The ligand is preferably a polydentate amine, and specific examples thereof include bidentate to hexadentate ligands. Among these, examples thereof preferably include a bidentate ligand, more preferably include 2,2-bipyridyl, 4,4'-di-(5-nonyl)-2,2'-bipyridyl, N-(n-propyl) pyridylmethanimine, and N-(n-octyl) pyridylmethanimine, and more preferably include 2,2-bipyridyl. Examples of the reducing agent include an alcohol, an aldehyde, a phenol, and an organic acid compound, and preferably include an organic acid compound. Examples of the organic compound include citric acid, oxalic acid, ascorbic acid, a salt of ascorbic acid, and an ascorbic acid ester, preferably include ascorbic acid, a salt of ascorbic acid, and an ascorbic acid ester, and more preferably include ascorbic acid. Specifically, a polymer chain extends from the polymerization initiating group 23a, a radical generation source, using the polymerizable monomer 35 as a substrate, the thickness of the polymer film increases, and the extending polymer chain also incorporates the polymerizable functional group 33 that is modifying the surface of the template 40 as a substrate when the extending polymer chain reaches the surface of the template 40, thereby a polymer is synthesized so that the concave 31 having a shape that conforms to the surface shape of the template 40 is formed. The polymer film can be grown to a thickness corresponding to about ½, preferably about ⅓ of the length from the top to the bottom of the template 40 (when the top of the drawing is the top) introduced into the base material 20. Thus, the polymer film 30 is obtained. As the reaction solvent in the polymerization reaction system, an aqueous solvent such as a buffer is preferably used from the viewpoint of, for example, inhibiting denaturation of the template 40.

[3-1-5. Removal Step]

As shown in FIG. 7, in the removal step, the first reversible linked group 22b and the second reversible linked group 32b are cleaved and converted into the group for binding antibody substance 22 and the group for binding signal substance 32, respectively, and the antibody substance 24 and the template 40 are removed. Because the second reversible linked group 32b is delivered only to the surface of the template 40 in the surface modification step above, in the concave 31 of the polymer film 30, the trace of the removed template 40, the group for binding antibody substance 22 remains inside and the group for binding signal substance 32 produced from the second reversible linked group 32b is placed only inside the concave 31. Thus, the base material for producing a sensor for analysis 10 is obtained.

[3-2. When Artificial Particle is Used as Template]

In addition to the exosome above, an artificial particle can be used as a template. When an artificial particle is used, the base material for producing a sensor for analysis of a detection target can be manufactured according when an exosome is used as a template above. Using an artificial particle is suitable for industrial production because it does not need an antibody to immobilize the template onto a base plate, and the base material can be manufactured at low cost. Because the artificial particle used for the template itself is an industrial product and the particle size is controlled, size control and homogenization of the concave formed in the base material for producing a sensor for analysis are easy, and thus a sensor for analysis excellent in analytical property can be produced from the obtained base material for producing a sensor for analysis.

The manufacturing method of a base material for producing a sensor for analysis of a detection target when an artificial particle is used as a template can include a molecular film-forming step of forming on a base material a molecular film having a binding functional group and a polymerization initiating group on a surface of the molecular film; a template introduction step of introducing an artificial particle as a template via a first reversible linked group to the binding functional group; a surface modification step of modifying a surface of the template with a polymerizable functional group via a second reversible linked group; a polymerization step of forming a polymer film on a surface of the base material by adding a polymerizable monomer and synthesizing a molecularly imprinted polymer corresponding to a part of the surface of the template using the polymerizable monomer as a substrate and the polymerization initiating group as a polymerization initiator; and a removal step of cleaving the first reversible linked group and the second reversible linked group to convert the first reversible linked group and the second reversible linked group into a group for binding antibody substance and a group for binding signal substance, respectively, and removing the template.

Figure 8:
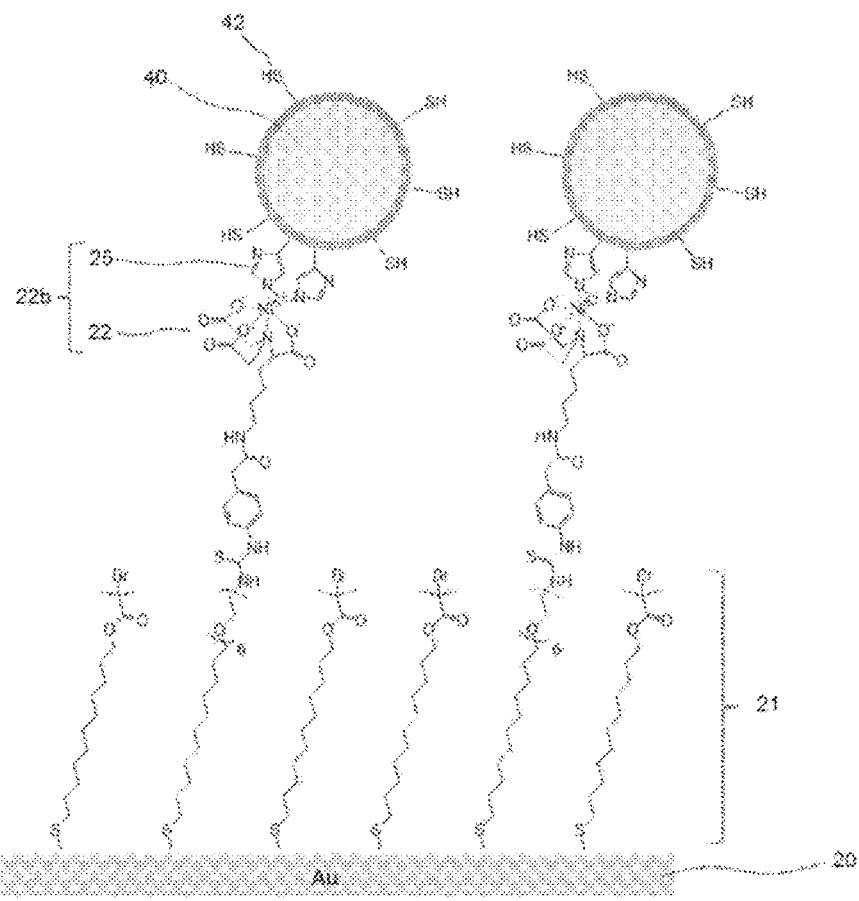
FIG. 8 shows a schematic diagram describing a template introduction step in the manufacturing method of a base material for producing a sensor for analysis of a detection target of the present invention (when an artificial particle is used as a template).
Figure 9:
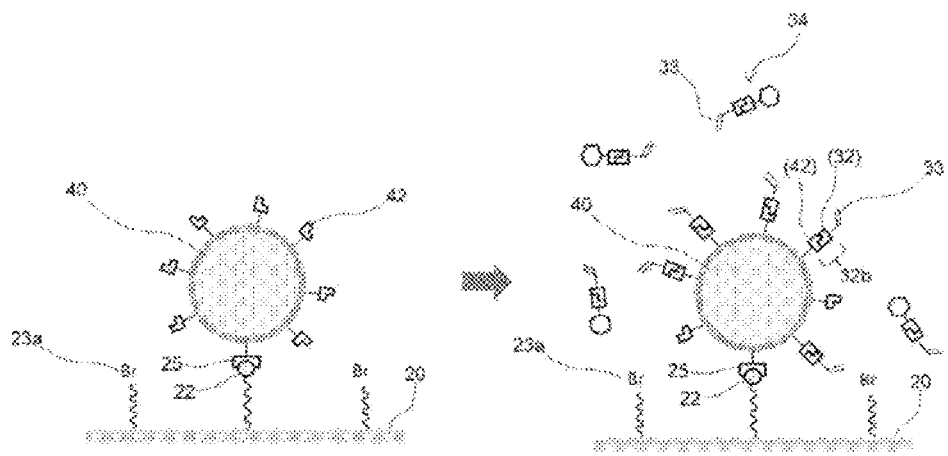
FIG. 9 shows a schematic diagram describing a surface modification step subsequent to FIG. 8 (when an artificial particle is used as a template).
Figure 10:
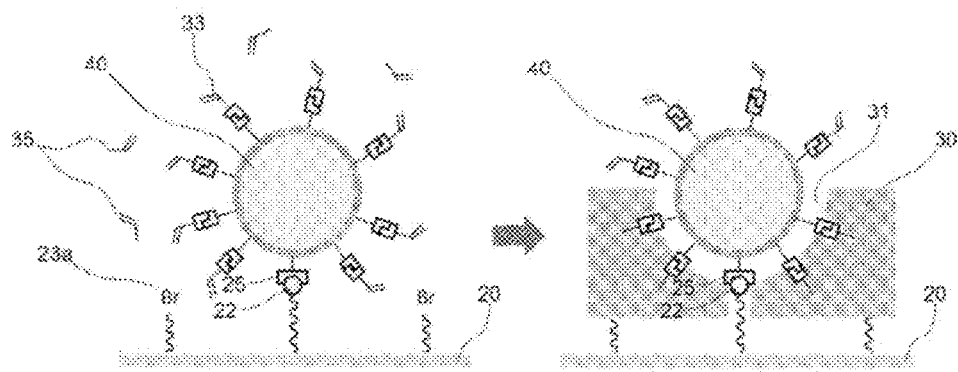
FIG. 10 shows a schematic diagram describing a polymerization step subsequent to FIG. 9 (when an artificial particle is used as a template).
Figure 11:
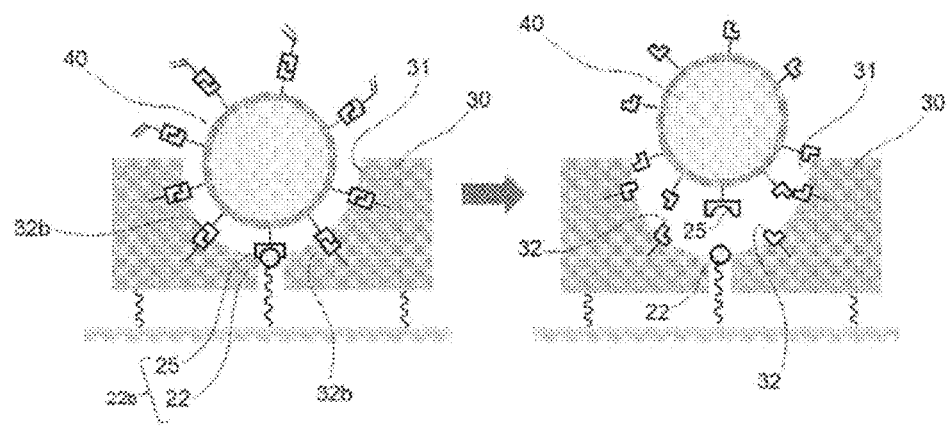
FIG. 11 shows a schematic diagram describing a removal step subsequent to FIG. 10 (when an artificial particle is used as a template).

The manufacturing method of the base material for producing a sensor for analysis of a detection target of the present invention when an artificial particle is used as a template is schematically shown in FIGS. 8 to 11. FIG. 8 shows the template introduction step, FIG. 9 shows the surface modification step, FIG. 10 shows the polymerization step, and FIG. 11 shows the removal step.

[3-2-1. Molecular Film-Forming Step]

The molecular film-forming step is the same as that when an exosome is used as a template, and specifically, it is as described in "3-1-1. Molecular film-forming step" and FIG. 3.

[3-2-2. Template Introduction Step]

As shown in FIG. 8, in the template introduction step, an artificial particle is introduced as the template 40 via a first reversible linked group 22b to the binding functional group 22a. The binding functional group 22 and the first reversible linked group 22b are as described in "3-1-1. Molecular film-forming step" and "3-1-2. Template introduction step"

above, respectively. In the illustrated aspect, the binding functional group 22a is an amino group, and the first reversible linked group 22b is a group formed by binding of a nitrilotriacetic acid (NTA) group (a type of group for binding antibody substance 22) to a histidine tag (a type of the group 25 capable of forming a first reversible linked group 22b by binding to the group for binding antibody substance 22).

The artificial particle used as the template 40 is not particularly limited as long as it can be used as a template, and examples thereof include an artificially manufactured inorganic particle and organic particle. Examples of the inorganic particle include a metal, a metal oxide, a nitride, a fluoride, a sulfide, a boride, a complex compound thereof, and hydroxyapatite, and preferably include silicon dioxide (silica). Examples of the organic particle include a latex cured product, dextran, chitosan, polylactic acid, poly (meth)acrylic acid, polystyrene, and polyethyleneimine. Because the size of the concave 31 (see FIG. 1 and the like) depends on the size of the template 40, the size of the artificial particle can be appropriately determined according to the size of the detection target. To form the concave 31 for receiving the detection target of interest, an artificial particle having a size same as or larger than the detection target can be used. For example, the size of the artificial particle can be selected from 1 nm to 10 μm.

The template 40 as an artificial particle includes on its surface a group 25 capable of forming the above-mentioned first reversible linked group 22b by binding to the above-mentioned group for binding antibody substance 22 and a reversible bond group 42 capable of forming the above-mentioned second reversible linked group 32b by binding to the above-mentioned group for binding signal substance 32. The group for binding antibody substance 22, the first reversible linked group 22b, the group 25 capable of forming a first reversible linked group 22b by binding to the group for binding antibody substance 22, the second reversible linked group 32b, and the reversible linked group 42 are as described above, and in the illustrated aspect, the group for binding antibody substance 22 is a nitrilotriacetic acid (NTA) group, the group 25 capable of forming a first reversible linked group 22b by binding to the group for binding antibody substance 22 is a histidine tag, and the reversible linked group 42 is a thiol group. The reversible linked group 42 shown as a thiol group binds to the group for binding signal substance 32 to form a second reversible linked group 32b. The method of modifying the surface of the artificial particle with a specific group in this way is widely known, and thus those skilled in the art can appropriately introduce the group 25 and the reversible bond group 42 to be introduced based on a known surface modification method, considering the type of those groups and components of the artificial particle.

Thus, by binding the template 40 having a histidine tag as the group 25 and a thiol group as the reversible bond group 42 on the surface of the artificial particle, the template 40 of the artificial particle is introduced into the amino group, the binding functional group 22a on the base material 20, via the first reversible linked group 22b.

[3-2-3. Surface Modification Step]

As shown in FIG. 9, in the surface modification step, the surface of the template 40 is modified with a polymerizable functional group 33 via a second reversible linked group 32b. More specifically, the reversible binding group 42 on the surface of the template 40 is converted into the second reversible linked group 32b and the polymerizable functional group 33 is introduced. The polymerizable functional group 33 is as described in "3-1-3. Surface modification step" above. In the illustrated aspect, an aspect is illustrated in which by disulfide exchange from a molecule including a (meth)acrylic group as a polymerizable functional group 33 and a disulfide bond 34 to the thiol group, a second reversible binding group 42 on the surface of the template 40, the thiol group is converted into a disulfide group, the second reversible linked group 32b, and the surface of the template 40 is modified with the polymerizable functional group 33. In the case where an artificial particle is used as the template 40, by using a template 40 having a thiol group, the second reversible binding group 42, on the surface in advance, the second reversible linked group 32b can be formed only on the surface of the template 40.

[3-2-4. Polymerization Step]

As shown in FIG. 10, in the polymerization step, the polymerizable monomer 35 is added, and a molecularly imprinted polymer corresponding to a part of the template 40 is synthesized using the polymerizable functional group 33 and the polymerizable monomer 35 as a substrate and the polymerization initiating group 23a as a polymerization initiator. Thus, the polymer film 30 including the concaves 31 is formed on the surface of the base material 20. The polymerizable monomer 35 and the polymer film 30 are as described in "3-1-4. Polymerization step" above.

[3-2-5. Removal Step]

As shown in FIG. 11, in the removal step, the first reversible linked group 22b and the second reversible linked group 32b are cleaved and converted into the group for binding antibody substance 22 and the group for binding signal substance 32, respectively, and the template 40 is removed. Because the second reversible linked group 32b is formed only on the surface of the template 40 in the surface modification step above, in the concave 31 of the polymer film 30, the trace of the removed template 40, the group for binding antibody substance 22 remains inside and the group for binding signal substance 32 produced from the second reversible linked group 32b is placed only inside the concave 31. Thus, the base material for producing a sensor for analysis 10 is obtained.

[4. Manufacturing of Sensor for Analysis of Detection Target]

The sensor for analysis of a detection target 50 is produced by only binding an antibody substance specific to the detection target 52 to the group for binding antibody substance 22, and binding a signal substance 53 to a group for binding signal substance 32 in the base material for producing a sensor for analysis 10.

The antibody-like substance 52 is not particularly limited as long as it is specific to the detection target, and the antibody-like substance 52 can be the same antibody-like substance as the antibody-like substance 24, or a different antibody-like substance from the antibody-like substance 24 used in manufacturing of the base material for producing a sensor for analysis 10.

Because the base material for producing a sensor for analysis 10 has a group for binding signal substance 32 only in the concave 31, which is a sensing place in the surface of the base plate 20, the signal substance 53 can be placed only in the concave 31.

For one base material for producing a sensor for analysis 10, one type of the antibody-like substance 52 and one type of the signal substance 53 can be introduced into all concaves 31, or one type of the antibody-like substance can be introduced into one concave 31 and another type of the antibody-like substance can be introduced into another concave 31, and different types of signal substances 53 can be introduced according to the types of antibody-like substances.

[5. Method for Analyzing Target Substance]

Figure 12:
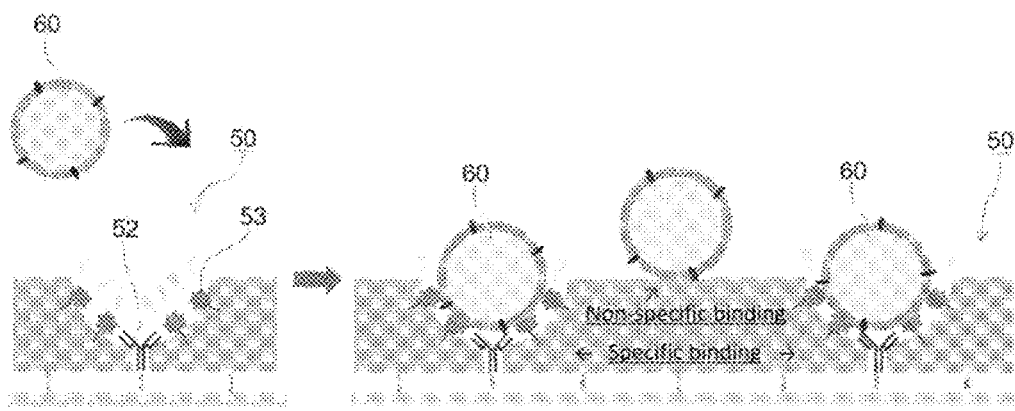
FIG. 12 shows a schematic diagram describing one example of a method for analyzing a detection target of the present invention.

FIG. 12 shows a schematic diagram describing one example of a method for analyzing a detection target of the present invention. As shown in FIG. 12, in the method for analyzing a detection target of the present invention, the analysis sample liquid containing the detection target 60 is contacted with the surface of the base material 20 of the sensor for analysis 50.

The detection target 60 is not particularly limited in principle as long as it is a substance that specifically binds to the antibody substance 52, and examples thereof include a low molecular weight substance, a protein, and a microparticle having a membrane structure as described above. Examples of the low molecular weight substance include any substances such as a hormone, an agent, a herbicide, an agricultural chemical, sugar, cholesterol, a lipid, uric acid, an environmental hormone, and a peptide. Examples of the protein include any proteins such as HSA, IgG, fibrinogen, transferrin, AST, ALT, LDH, ALP, LAP, γ-GTP, CRP, AFP, and PSA. Examples of the microparticle having a membrane structure include an extracellular microparticle, an intracellular vesicle, an organelle, and a cell. Examples of the membrane structure include a lipid bilayer membrane structure. Examples of the extracellular microparticle include an exosome, a microvesicle, and an apoptotic body. Examples of the intracellular vesicle include a lysosome and an endosome. Examples of the organelle include a mitochondrion. Examples of the cell include a cancer cell such as a circulating tumor cell (CTC) and other disease-related cells.

Though the aspect of the analysis sample liquid containing the detection target 60 is not particularly limited, the analysis sample liquid is preferably one that has not undergone the treatment that separates the detection target 60 from the viewpoint of swiftness. Examples of the treatment that separates the detection target 60 include ultracentrifugation, ultrafiltration, continuous flow electrophoresis, filtration with a size filter, and gel filtration chromatography.

The analysis sample liquid containing the detection target 60 can be a sample obtained in an environment in which the detection target 60 is present (when the detection target 60 is a cell or an extracellular microparticle), or a sample obtained in an environment in which the detection target 60 can be produced (when the detection target 60 is an extracellular particle and is a product from a cell). Specifically, the analysis sample liquid can be a biological sample containing a cell. When the detection target 60 is an extracellular microparticle such as an exosome, examples of the cell that produces the detection target 60 include a cancer cell, a mast cell, a dendritic cell, a reticulocyte, an epithelial cell, a B cells, and a nerve cell. More specifically, examples of the analysis sample liquid containing the detection target 60 include body fluids such as blood, milk, urine, saliva, lymph, cerebrospinal fluid, amniotic fluid, tear fluid, sweat, and rhinorrhea, and further include a treated liquid obtained by subjecting these body fluids to a pretreatment such as removal of unnecessary components and a culture solution obtained by culturing cells contained in these body fluids. Among these analysis sample liquids, body fluids such as urine, saliva, tear fluid, sweat, and rhinorrhea are particularly preferred in terms of non-invasiveness and easy collection.

When the analysis sample liquid containing the detection target 60 is contacted with the surface of the base material 20 of the sensor for analysis 50, the detection target 60 is specifically captured by the antibody substance 52 in the concave 31. For example, when the detection target 60 is an exosome, the exosome is captured by specific binding to the antibody substance 52 via a membrane protein (an exosome-specific antigen), for example, CD63, CD9, CD81, CD37, CD53, CD82, CD13, CD11, CD86, ICAM-1, Rab5, Annexin V, and LAMP1. When the detection target 60 is a cancer cell, the cancer cell is captured by specific binding to the antibody substance 52 via a cancer cell-specific antigen, for example, Caveolin-1, EpCAM, FasL, TRAIL, Galectine 3, CD151, Tetraspanin 8, EGFR, HER2, RPN2, CD44, and TGF-β.

In the moment when the detection target 60 is specifically captured by the antibody substance 52 in the concave 31, the signal substance 53 is shielded by the detection target 60, and thus the signal intensity detected from the signal substance 53 is reduced. The detection target 60 is detected by the signal intensity change. Because the capture of the detection target 60 and the signal intensity change occur almost simultaneously, there is no need to add a reagent for the detection of the detection target 60, and the detection can be performed quickly.

In the case where the sensor for analysis 50 is configured so that the signal substance 53 will be one of the fluorescent dye pair that cause fluorescence resonance energy transfer (FRET), and the other of the fluorescent dye pair will be bound to the detection target 60 in advance, in the moment when the detection target 60 is specifically captured by the antibody substance 52 in the concave 31, the fluorescent dye in the signal substance 53 and the fluorescent dye in the detection target 60 are close to each other, and thus fluorescence is emitted by FRET. The detection target 60 is detected by the fluorescence emission by the FRET. Because the capture of the detection target 60 and the fluorescence emission by the FRET occur almost simultaneously, there is no need to add a reagent for the detection of the detection target 60, and the detection can be performed quickly. The fluorescent dye pair that causes FRET is not particularly limited, and a donor dye or an acceptor dye can be selected as the signal substance 53 without limitation. Preferably, a donor dye can be selected as the signal substance 53. Specific examples of donor/acceptor dyes that constitute the fluorescent dye pair that causes FRET include fluorescein isothiocyanate (FITC)/tetramethylrhodamine isothiocyanate (TRITC), Alexa Fluor647/Cy5.5, HiLyte Fluor647/Cy5.5, and R-phycoerythrin (R-PE)/allophycocyanin (APC).

Further, because the sensor for analysis 50 of the present invention has no signal substance 53 in the part other than the concave 31 on the surface of the base material 20, the sensor is not affected by an undesired background even if there is non-specific adsorption in the part other than the concave 31 on the surface of the base material 20. Thus, the detection target 60 can be detected with high sensitivity.

EXAMPLES

Though the present invention will be described in detail below based on Examples, the present invention is not limited thereto.

Example 1: Base Material for Producing Sensor for Analysis of Detection Target when Exosome is Used as Template In this example, a mixed self-assembled monolayer (mixed SAMs) having an amino group and a bromo group at the end on a gold thin film deposited glass base plate was produced (molecular film-forming step), an NTA group was introduced into the amino group at the end to form a NTA-Ni complex, then an antibody binding protein Protein G was bound by chelate bond, an Anti-CD9 antibody was immobilized, and further, an exosome was immobilized via the Anti-CD9 antibody (template introduction step). Then, the exosome membrane was modified with a methacrylic group using BAM (surface modification step), and a polymer thin film was synthesized by surface-initiated living radical polymerization (polymerization step). Finally, the exosome was removed (removal step) to obtain a base material for producing a sensor for analysis of a detection target.

1. Production of Mixed SAMs (Molecular Film-Forming Step)

Concentrated sulfuric acid and 30 w/v % hydrogen peroxide water were mixed at 3:1 (volume basis) to prepare a piranha solution. A gold thin film deposited glass base plate (SIA Kit Au from GE Healthcare was used when SPR measurement was performed, and a gold deposited mirror from JASCO Corporation was used when fluorescence measurement was performed) was immersed in a piranha solution at room temperature for 15 minutes to remove organic residues. The base plate was washed with pure water, then immersed in an EtOH solution of 0.5 mM Amino-EG6-undecanthiol hydrochloride (Dojindo Molecular Technologies, Inc.), 0.5 mM Bis [2-(2-bromoisobutyryloxy) undecyl] disulfide (Sigma-Aldrich Co. LLC), and allowed to stand at 25° C. for 24 hours.

2. Immobilization of Exosome Via Protein G and Anti-CD9 Antibody (Template Introduction Step)

Onto the base plate, 80 μL of 20 mM Isothiocyanobenzyl-NTA (Dojindo Molecular Technologies, Inc.) DMSO solution was dropped, and the base plate was allowed to stand at 25° C. for 2 hours. The base plate was washed with DMSO and pure water, then 100 μL of 4 mM $NiCl_2$ aqueous solution was dropped onto the base plate, and the base plate was allowed to stand at room temperature for 15 minutes. The base plate was washed with pure water, then 100 μL of 100 μM Recombinant His-tagged Protein G (BioVision Inc.) PBS (10 mM phosphate, 140 mM NaCl, pH 7.4) solution was dropped onto the base plate, and the base plate was allowed to stand at 25° C. for 30 minutes. The base plate was washed with PBS, then 100 μL of 0.3 UM Anti-CD9 (Human) mAb (MEDICAL & BIOLOGICAL LABORATORIES CO., LTD.) PBS (10 mM phosphate, 140 mM NaCl, pH 7.4) solution was dropped onto the base plate, and the base plate was allowed to stand at 25° C. for 30 minutes. Thus, the Protein G and Anti-CD9 antibody were immobilized. Immobilization of protein G and Anti-CD9 antibody was confirmed by the increase in SPR signal (response unit RU) (ΔRu was 4500 for Protein G and 5919 for Anti-CD9) using surface plasmon resonance analysis (measurement conditions: sample 1:100 μM Protein G, sample 2:0.3 UM Anti-CD9, flow rate: 30 μL/min, injection volume: 30 μL, running buffer: PBS (10 mM phosphate, 140 mM NaCl, pH 7.4), temperature: 25° C.). For the surface plasmon resonance analysis, a surface plasmon resonance intermolecular interaction analyzer Biacore Q (GE Healthcare) was used (hereinafter, the same applies when SPR analysis was performed).

Further, the base plate was washed with PBS, then 100 μL of 20 μg/mL exosome (Exosomes from PC3 cell, HansaBioMed Life Sciences) PBS (10 mM phosphate, 140 mM NaCl, pH 7.4) solution was dropped onto the base plate, and the base plate was allowed to stand at 25° C. for 30 minutes. Thus, the exosome was immobilized. The immobilization of the exosome was confirmed as follows: a base plate same as above except that the Anti-CD9 antibody was not immobilized was separately produced, the binding behaviors of exosomes of both base plates were compared using SPR (measurement conditions: sample: exosome, concentration: 25, 50, 100, 250, 500, 1000, 2500, 5000, 10000 ng/mL, flow rate: 10 μL/min, injection volume: 30 μL, running buffer: PBS (10 mM phosphate, 140 mM NaCl, pH 7.4), temperature: 25° C.), and the base plate on which the Anti-CD9 antibody was immobilized was found to have a larger amount of exosome adsorption.

3. Modification of Exosome with Methacrylic Group (Surface Modification Step)

3-1. Synthesis of Anchoring Substance BAM-SH (Corresponding to the Anchoring Substance 41 in FIG. 5)

BAM (Biocompatible Anchor for cell Membrane (Mw=2000); SUNBRIGHT OE-020CS, YUKA SANGYO CO., LTD.) (10.3 mg) (5.65 μmol) and 2-Aminoethanethiol hydrochloride (Tokyo Chemical Industry Co., Ltd.) (31.9 mg) (280 μmol, 49.7 eq) were dissolved in PB (10 mM phosphate, pH 7.0) (50 ML), and reacted at 25° C. for 4 hours to obtain an anchoring substance BAM-SH. The buffer of pH 7.0 was used to decrease the hydrolysis rate of the NHS group of BAM and increase the reactivity with the amino group.

[Chemical Formula 2]

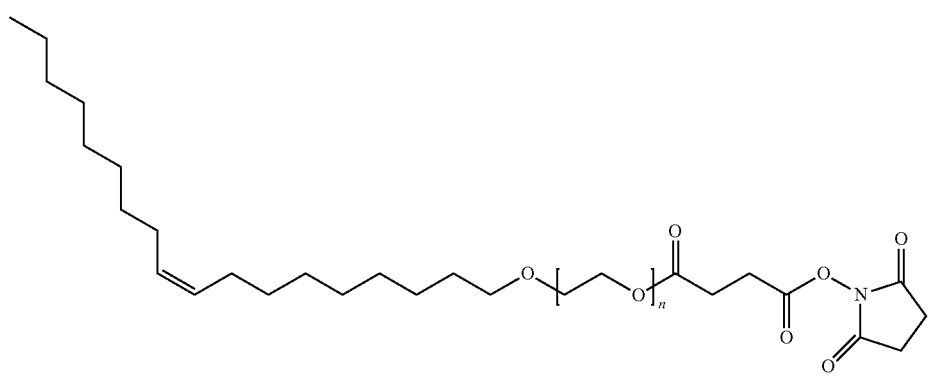

BAM: Biocompatible Anchor for Cell Mebrane (Mw = 2000)

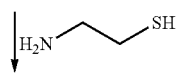

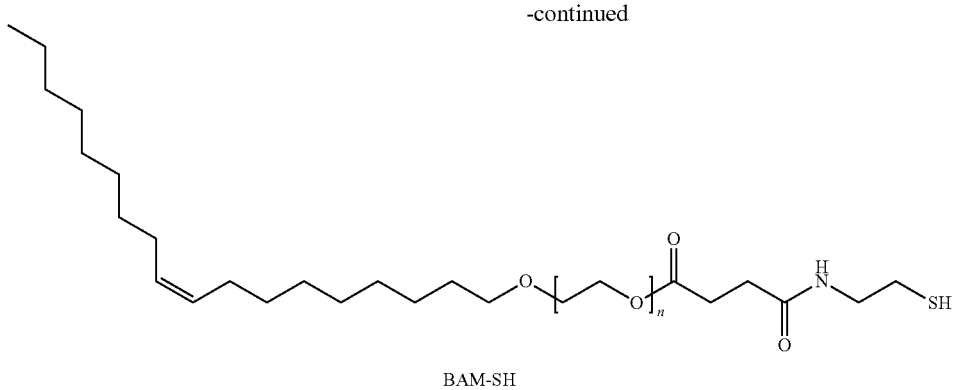

BAM-SH 3-2. Synthesis of 2-(2-pyridyl) dithioethyl methacrylate (Corresponding to Molecule 34 in FIG. 5)

2,2-Dipyridyl disulfide (1.545 g, 7.01 mmol) was dissolved in methanol (15 mL), 180 μL of acetic acid was added, and the mixture was stirred. 2-Mercaptoethanol (600 μL, 8.45 mmol) dissolved in methanol was added gradually at room temperature, and the mixture was allowed to react overnight. The fraction at Rf=0.33 was collected by silica gel chromatography (EtOAc:hexane=50:50 (volume basis)) and distilled under reduced pressure to obtain a pale yellow, transparent oily purified product (2-hydroxyethyl 2-pyridyl disulfide)

2-Hydroxyethyl 2-pyridyl disulfide (1.028 g, 5.49 mmol), Methacrylic Acid (0.70 mL, 8.23 mmol, 1.5 eq), WSC—HCl (1.5825 g, 8.23 mmol, 1.5 eq), and DIEA (0.956 mL 8.23 mmol), 1.5 eq) were dissolved in an appropriate amount of methanol, and the mixture was stirred at room temperature and allowed to react for 3 days. The collected organic phase was washed with saturated saline and pure water, and then dehydrated with $Na_2SO_4$. After the removal of the solvent, the fraction at Rf=0.37 was collected by silica gel chromatography (EtOAc:hexane=20:80 (volume basis)) and distilled under reduced pressure to obtain a brown, transparent oily purified product (2-(2-pyridyl) dithioethyl methacrylate). ($^1$H-NMR (CDCl$_3$, 300 MHZ), δ (ppm): 8.48 (m, 1H, aromatic proton ortho-N), 7.60-7.71 (m, 2H, 9 aromatic proton meta-N and para-N), 7.11 (m, 1H, aromatic proton, orthodisulfide linkage), 6.22 (d, 1H, vinylic proton, cis-ester), 5.59 (d, 1H, vinylic proton, trans-ester) 4.41 (t, 2H, —S—S—CH$_2$CH$_2$O—), 3.12 (t, 2H, —S—S—CH$_2$CH$_2$O—), 1.92 (s, 3H, methyl proton of the methacryloyl group))

[Chemical Formula 3]

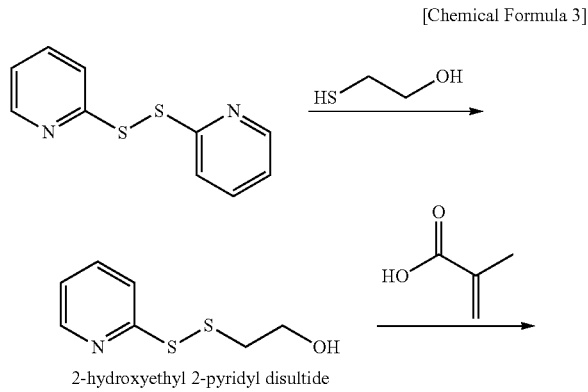

2-(2-Pyridyl)dithioethyl methacrylate

BAM-SH was diluted with PB to obtain a PB (10 mM phosphate, pH 7.0) solution of 100 μM BAM-SH. The exosome-immobilized base plate was immersed in the solution, allowed to stand at 25° C. for 1 hour, and washed with PBS (10 mM phosphate, 140 mM NaCl, pH 7.4). Then, 2-(2-pyridyl) dithioethylmethacrylate was dissolved in 50 μL of DMSO, then the solution was diluted to 100 μM with PBS (10 mM phosphate, 140 mM NaCl, pH 7.4) (DMSO occupied about 0.9 wt % of the total) to prepare a PBS (pH 7.4) solution of 100 μM 2-(2-pyridyl) dithioethylmethacrylate. The base plate was immersed in the prepared solution and allowed to react overnight at 25° C.

4. Production of MIP Thin Film (Polymerization Step)

According to the recipe shown in the table below (Recipe of SI-ATRP for synthesis of Exosome-MIP), a polymer thin film was synthesized by surface-initiated atom transfer radical polymerization (SI-ATRP).

TABLE 1

| Recipe of SI-ATRP for synthesis of Exosome-MIP | |
|---|---|
| MPC | 50 mM |
| 2,2'-Bipyridyl | 2 mM |
| CuBr$_2$ | 1 mM |
| L-Ascorbic Acid | 0.5 mM |
| PBS (10 mM posphate, 140 mM NaCl, pH 7.4) | 10 mL |

In a 25 mL Schlenk flask, a solution consisting of 2-methacryloyloxyethyl phosphorylcholine (MPC), 2,2'-bipyridyl (NACALAI TESQUE, INC.), CuBr$_2$ (NACALAI TESQUE, INC.) and PBS (10 mM phosphate, 140 NaCl, pH 7.4) was prepared and degassed, and then the base plate was immersed. The solution was degassed again, and then L-Ascorbic Acid (L(+)-Ascorbic Acid, NACALAI TESQUE, INC.) was injected with a syringe to initiate polymerization. The polymerization condition was 1 hour in a 40° C. water bath, and shaking was continued at low speed during the polymerization reaction.

5. Removal of Exosome and Antibody (Removal Step)

The base plate was immersed in 1 M EDTA-4Na aqueous solution for 15 minutes to remove $Cu^{2+}$. The base plate was immersed in 50 mM TCEP aqueous solution at 25° C. for 3 hours to reduce disulfide bonds. The base plate was washed with pure water, then immersed in 50 mM acetate buffer (pH 4.0) containing 0.5 wt % SDS, and shaken at low speed for 1 hour to cut out the Protein G, the Anti-CD9, and the exosome from the polymer thin film. The fact that the exosome was actually cut off was confirmed by the decrease in SPR signal (response unit Ru) using SPR (measurement conditions: sample 1:50 mM TCEP aqueous solution×3, sample 2: acetate buffer (10 mM, pH 4.0), 0.5 wt % SDS solutions×2, flow rate: 30 µL/min, injection volume: 30 µL, running buffer: PBS (10 mM phosphate, 140 mM NaCl, pH 7.4), temperature: 25° C.). Thus, a base material for producing a sensor for analysis of a detection target (MIP base plate) was obtained.

Example 2: Sensor for Analysis of Detection Target when Exosome is Used as Template To the base material for producing a sensor for analysis (MIP base plate) obtained in Example 1, 100 µL of 4 mM $NiCl_2$ aqueous solution, 100 µL of 100 µM Protein G PBS (10 mM phosphate, 140 mM NaCl, pH 7.4) solution, and 100 µL of Anti-CD9 antibody 0.3 µM PBS (10 mM phosphate, 140 mM NaCl, pH 7.4) solution were dropped to immobilize the Anti-CD9 antibody. Further, 100 µL of 500 µM POLARIC-MLI (GORYO Chemical, Inc.) DMSO solution was dropped onto the base plate, and the base plate was allowed to stand at 25° C. for 1 hour and then washed. Thus, the sensor for analysis of a detection target was obtained.

Figure 13:
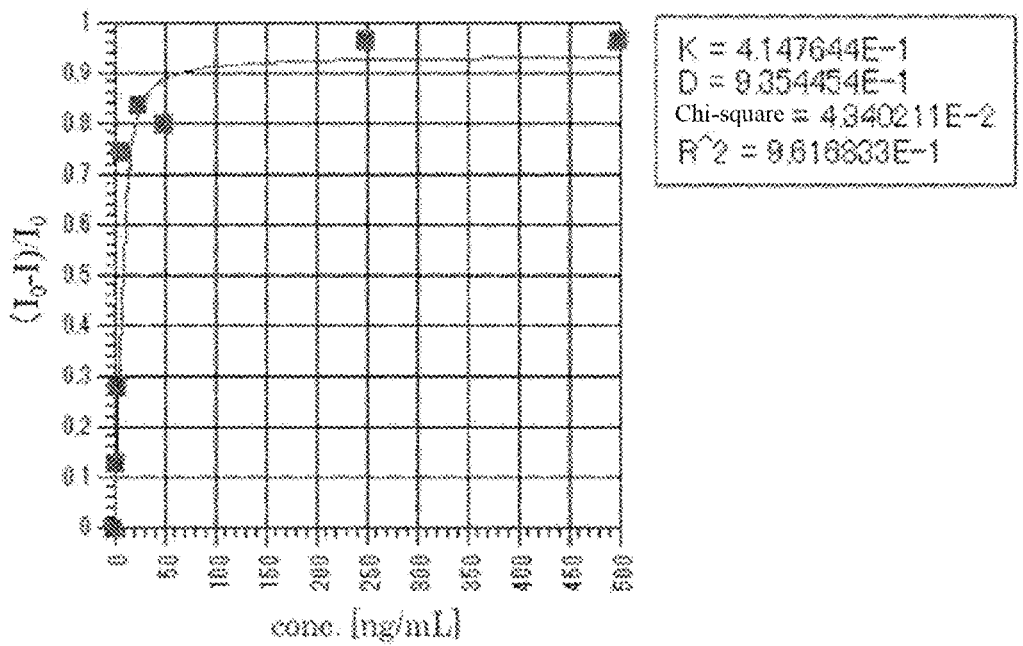
FIG. 13 shows a graph of logarithmic display of the fluorescence intensity change with respect to the exosome concentration, and its curve fitting result, obtained in exosome detection by fluorescence analysis using the sensor for analysis of the present invention (produced using an exosome as a template) in Example 3.

Example 3: Exosome Detection by Fluorescence Analysis Using Sensor for Analysis of Detection Target Using the sensor for analysis obtained in Example 2, the binding behavior of the exosome was observed. Specifically, 10 µL each of exosome (estimated average molecular weight: $1.92 \times 10^8$ Da) solutions with different concentrations were dropped onto the produced base plate, and the base plate was covered with an 18×18 mm cover glass and allowed to stand at room temperature for 10 minutes. The base plate was allowed to stand with being shaded. The fluorescence intensity of the base plate after the reaction was measured. A fluorescence microscope (inverted research microscope IX 73 (Olympus Corporation)) was used for the measurement of fluorescence intensity, the measurement conditions were as follows: concentration: 2.5, 5, 10, 50, 100, 250, 500, 1000, 2500, 5000 ng/mL, filter: BW, objective lens: ×10, exposure time: 0.50 sec, and amount of light: 100%, and the average value from 5 points was taken as the measurement value. Andor SOLIS was used as the spectroscopic software. The fluorescence intensity change (($I_o$–I)/$I_o$) with respect to the exosome concentration was measured to create a graph, which was subjected to curve fitting (regression analysis) to calculate the binding constant. The results are shown in FIG. 13. Graph creation software DeltaGraph was used for graph creation and curve fitting, and the binding constant was calculated by the following equation. As a result, the binding constant Ka was calculated to be $1.50 \times 10^{14}$ [$M^{-1}$].

$$Y = \{(1 + K \times G + K \times H) - \qquad \text{[Equation 1]}$$

-continued
$$((1 + K \times G + K \times H)^2 - 4 \times K \times K \times H \times G)^{1/2}\} \times \frac{D}{2KG}$$

Figure 14:
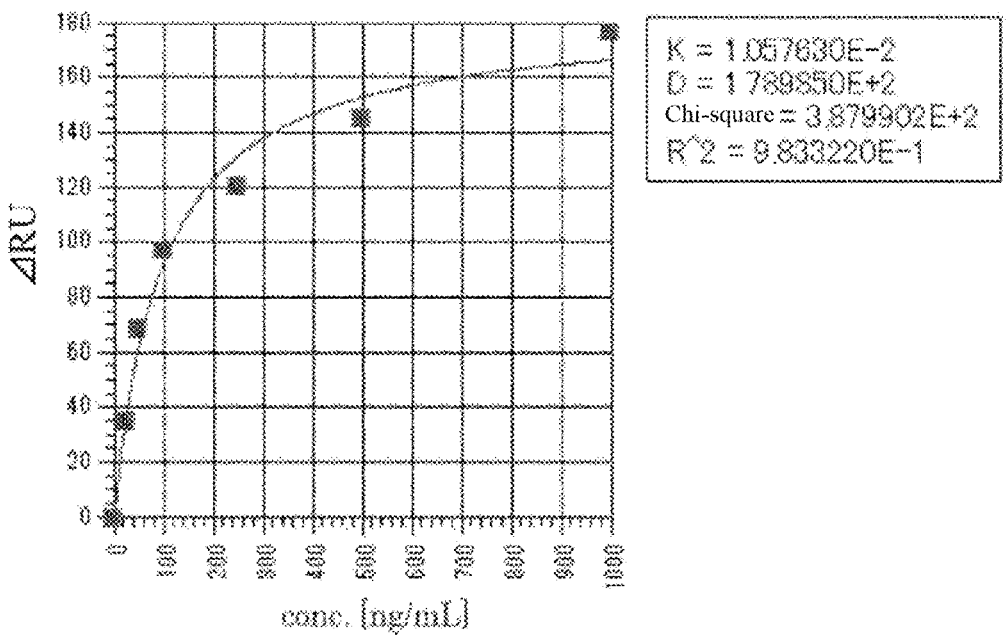
FIG. 14 shows a graph showing the SPR signal change with respect to the exosome concentration, and its curve fitting result, obtained in exosome detection by SPR using the sensor for analysis of the present invention (produced using an exosome as a template) in Reference Example.

Y: Fluorescence intensity change, H: Exosome concentration, G: Initial concentration of host molecule Reference Example: Exosome Detection by SPR Using Sensor for Analysis of a Detection Target Using the sensor for analysis obtained in Example 2, the binding constant was determined by surface plasmon resonance (SPR) analysis. SPR measurement conditions were as follows: sample: exosome, concentration: 25, 50, 100, 250, 500, 1000, 2500, 5000 ng/mL, flow rate: 10 µL/min, injection volume: 30 µL, running buffer: PBS (10 mM phosphate, 140 mM NaCl, pH 7.4), and temperature: 25° C. A graph showing the SPR signal (response unit RU) with respect to the exosome concentration was subjected to curve fitting in the same manner as in Example 3 to calculate the binding constant. The results are shown in FIG. 14. As a result, the binding constant Ka was calculated to be $2.03 \times 10^{12}$ [$M^{-1}$]. The reason why the calculated binding constant was larger than that in Example 3 is as follows: in Example 3, fluorescence change only in the concave, which is a sensing place, was specifically detected and even if there was non-specific adsorption in the part other than the sensing place, the non-specific adsorption did not affect the detection results, while in this Reference Example, in addition to the adsorption in the sensing place, the non-specific adsorption in the part other than the sensing place was also detected due to the principle of SPR analysis. Thus, according to the present invention, only the specifically recognized target can be detected.

Figure 15:
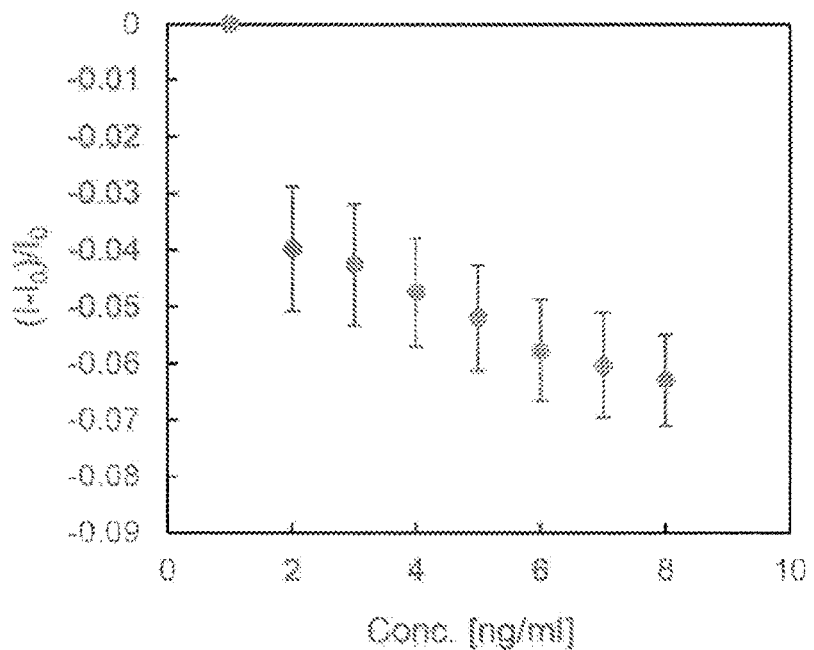
FIG. 15 shows a graph showing the fluorescence intensity change with respect to the exosome concentration, obtained in reproducibility test of the production of the sensor for analysis of the present invention (produced using an exosome as a template) in Example 5.

Example 5: Reproducibility of Production of Sensor for Analysis of Detection Target Three sensors for analysis of a detection target were produced by the same method as in Example 2. Onto the three sensor for analysis of a detection target produced, exosome solutions with different concentrations were dropped and reacted by the same method as in Example 3, to measure the fluorescence intensity after the reaction. The fluorescence intensity was measured at 3 points for each sensor for analysis, 9 points in total. The fluorescence intensity change at 9 measurement points is shown in FIG. 15. In FIG. 15, the horizontal axis indicates the exosome concentration (ng/ml), and the vertical axis indicates the fluorescence intensity change (($I$–$I_0$)/$I_0$). As shown in FIG. 15, the measurement error between the sensors for analysis was small, indicating that the sensors were produced with good reproducibility.

Example 6: Exosome Detection by FRET Using Sensor for Analysis of Detection Target 1. Rhodamine Labeling of Exosome
(1) Synthesis of Thiolated BAM (BAM-SH)
In 50 µL of PBS (pH 7.0), 10 mg (5.6 µmol) of BAM (SUNBRIGHT OE-020CS, Mw=2000) and 32 mg (280 µmol, 50 eq) of 2-aminoethanethiol hydrochloride were dissolved and reacted overnight at 25° C.

(2) Thiolation of Exosome Surface by Thiolated BAM

A solution (400 μL) obtained by diluting the obtained thiolated BAM solution 100-fold with 10 mM PBS (pH 7.4) and 2 μg/100 μL of exosome solution were mixed and reacted at 4° C. for 3 hours.

(3) Rhodamine Labeling of Exosome with Thiol-Reactive Rhodamine

The obtained reaction liquid was ultrafiltered (Amicon Ultra 0.5; 100 kDa) three times, 450 μL of 1 mM thiol-reactive rhodamine maleimide solution (10 mM PBS pH 7.4) was added to 27 μL of the collected solution, and the mixture was reacted in the dark at 4° C. for 3 hours.

(4) Purification of Rhodamine-Labeled Exosome by Dialysis

The rhodamine-labeled exosome was purified by dialysis at 4° C. for 24 hours using a dialysis membrane having a pore size of 10 kDa.

2. Production of Sensor for Analysis of Detection Target Labeled with Fluorescein A sensor for analysis of a detection target was produced in the same manner as in Example 2 except that 100 μM thiol-reactive fluorescein maleimide solution was dropped and the base plate was allowed to stand at room temperature for 3 hours instead of dropping 100 μL of 500 μM POLARIC-MLI (GORYO Chemical, Inc.) DMSO solution and allowing the base plate to stand at 25° C. for 1 hour.

3. Measurement of Rhodamine-Labeled Exosome by FRET Using a Fluorescein-Labeled Sensor The exosome solutions of 0, 5, 10, 50, 100, 500 ng/mL were dropped onto the sensor and reacted for 3 minutes, and the sensor was sufficiently washed with pure water and PBS. After washing, PBS was dropped, a cover glass was placed, and fluorescence intensity was measured under the following measurement conditions.

Measurement condition: Filter
Excitation: Filter for fluorescein
Fluorescence: Filter for rhodamine
Objective lens: ×40
Exposure time: 0.1 sec.

Figure 16:
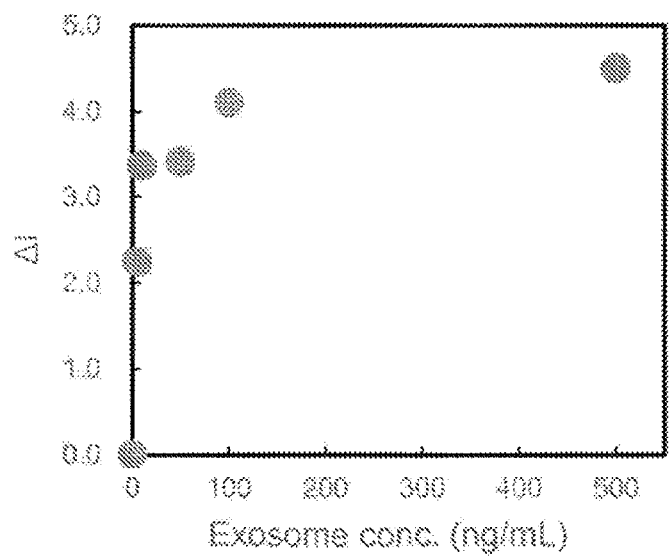
FIG. 16 shows a graph showing the fluorescence intensity change with respect to the exosome concentration, obtained in exosome detection by FRET using the sensor for analysis of the present invention (produced using an exosome as a template) in Example 6.

The measurement results are shown in FIG. 16. In FIG. 16, the horizontal axis indicates the exosome concentration, and the vertical axis indicates the amount of change in fluorescence intensity (ΔI). As shown in FIG. 16, rhodamine fluorescence was observed at the excitation wavelength of fluorescein (that is, FRET was confirmed). FRET does not occur when fluorescein and rhodamine are not placed in close proximity to each other, and thus it was shown that the exosome actually bound to the fluorescein-labeled concave in the sensor for analysis.

Example 7: Binding Inhibition Test of Exosome by Addition of Free Anti-CD9 Antibody In this example, to confirm that the exosome binds to the concave in the sensor for analysis via an antibody, the change in the binding behavior of the exosome when the free antibody coexists at the time of dropping the exosome was examined.

First, a sensor for analysis of a detection target was produced in the same manner as in Example 2 except that Alexa Fluor™ 647 was used instead of POLARIC-MLI. Next, 0.01, 0.05, 0.1, 0.5, 1, 5, and 10 ng/ml exosome PBS (10 mM phosphate, 140 mM NaCl, pH 7.4) solutions were prepared as samples in which free antibodies do not coexist, and 0.01, 0.05, 0.1, 0.5, 1, 5, and 10 ng/ml exosome PBS (10 mM phosphate, 140 mM NaCl, pH 7.4) solutions in which free antibodies coexist were prepared as samples in which free antibodies coexist by adding 100 μl of 0.3 UM Anti-CD9 antibody PBS (10 mM phosphate, 140 mM NaCl, pH 7.4) solution to 100 μl of 20 ng/ml exosome PBS (10 mM phosphate, 140 mM NaCl, pH 7.4) solution, incubating the mixture at 4° C. for 1 hour, and diluting the obtained solution with PBS.

Figure 17:
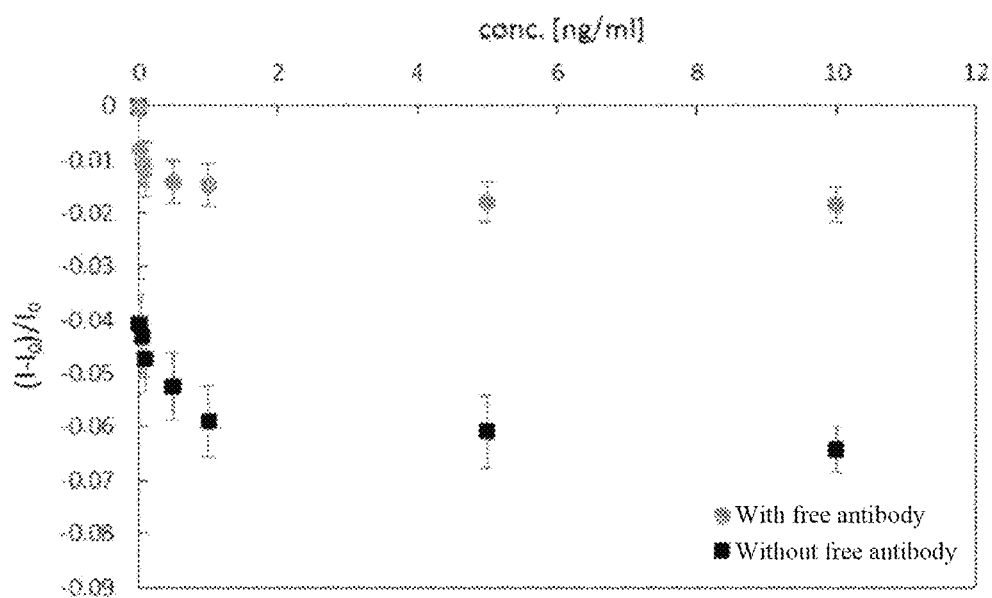
FIG. 17 shows a graph showing the fluorescence intensity change with respect to the exosome concentration in the sample when a free Anti-CD9 antibody is added, and when a free Anti-CD9 antibody is not added together with a sample to the sensor for analysis of the present invention (produced using an exosome as a template), obtained in the binding inhibition test of exosome by addition of a free Anti-CD9 antibody in Example 7.

The fluorescence intensity change was measured in the same manner as in Example 3 for each of the samples in which free antibodies do not coexist and the samples in which free antibodies coexist. The results are shown in FIG. 17. As shown in FIG. 17, it was found that exosome binding is inhibited when free antibodies coexist. This strongly suggests that exosome binding occurs via antibodies in the binding space. Thus, it was found that the antibody and the fluorescent dye are provided in the concave in the sensor for analysis, and the exosome binding information can be read out.

Example 8: Base Material for Producing Sensor for Analysis of a Detection Target when Silica Nanoparticle is Used as Template 1. Synthesis of Template-Synthesis of Silica Nanoparticle into which Thiol Group and Histidine Tag (His-Tag) are Introduced FITC-labeled silica nanoparticles (having 5 nmol of —COOH on the surface per 200 μl, and a particle size of 200 nm) (200 μl) were dispersed in dichloromethane (DCM) (silica nanoparticle dispersion). Ethyl (dimethylaminopropyl) carbodiimide (EDC: 50 nmol, 10 eq), N-hydroxysuccinimide (NHS: 50 nmol, 10 eq), and N,N-diisopropylethylamine (DIEA: 50 nmol, 10 eq) were dissolved in dry DCM, and mixed with the silica nanoparticle dispersion. The mixture was reacted overnight to modify the surface of the silica nanoparticles with NHS. A His-tag with 6 histidines linked by peptide bond (having a lysine residue at the end and having a free ε-amino group: 0.10 μmol, 40 eq) and 2-aminoethanethiol hydrochloride (0.1 μmol, 40 eq) were added to the surface-modified silica nanoparticles, and reacted at room temperature. After completion of the reaction, silica nanoparticles into which a thiol group and His-tag were introduced (SH/His-tagged silica nanoparticles) were purified by centrifugation and filtration.

2. Preliminary Experiment-Immobilization of SH/His-Tagged Silica Nanoparticles Via Ni-NTA and Detachment Thereof Onto the mixed SAMs obtained in Item 1 of Example 1, 20 mM Isothiocyanobenzyl-NTA (80 μL) (Dojindo Molecular Technologies, Inc.) DMSO solution was dropped, and the base plate was allowed to stand at 25° C. for 2 hours. The base plate was washed with DMSO and pure water, then 100 μL of 4 mM $NiCl_2$ aqueous solution was dropped onto the base plate, and the base plate was allowed to stand at room temperature for 15 minutes. The base plate was washed with pure water, then SH/His-tagged silica nanoparticles dispersed in 10 mM phosphate, 140 mM NaCl, pH 7.4, were dropped to obtain a base plate on which SH/His-tagged silica nanoparticles are immobilized. For comparison, a base plate onto which a dispersion of silica nanoparticles that were not subjected to His-tag modification was also dropped in the same manner was also obtained. For these base plates, the fluorescence intensity derived from the fluorescent molecule fluorescein (excitation: 480 nm/fluorescence: 510 nm) introduced into the silica nanoparticles before and 1 hour after dropping of the silica nanoparticles was measured to confirm the immobilization of silica nanoparticles. To confirm whether the bound silica nanoparticles are detached, the base plate was treated with an acidic buffer (0.5 wt % SDS 50 mM acetate buffer (pH 4.0)), and then the fluorescence intensity on the surface of the base plate was measured again.

TABLE 2

| Silica particle without His-tag modification (surface: —COOH) | |
|---|---|
| Fluorescence intensity before dropping of silica particle | 283.026 |
| Fluorescence intensity after dropping of silica particle | 292.363 |
| Silica particle with His-tag modification (surface: —SH, His-tag) | |
| Fluorescence intensity before dropping of silica particle | 272.131 |
| Fluorescence intensity after dropping of silica particle | 459.920 |
| Fluorescence intensity after acidic buffer treatment | 285.674 |

As shown in Table above, for the silica nanoparticles without His-tag modification and the silica nanoparticles with His-tag modification, the fluorescence intensity increased after dropping the silica nanoparticles with His-tag modification onto the base plate, which confirms the immobilization of silica nanoparticles. Further, in the silica nanoparticles with His-tag modification, after treatment with an acidic buffer (0.5 wt % SDS 50 mM acetate buffer (pH 4.0)), the fluorescence intensity decreased to the same level as that before dropping, and thus it was found that the silica nanoparticles bound via Ni-NTA were detached in the presence of acid and a surfactant.

3. Production of Base Material for Producing Sensor for Analysis of Detection Target when Silica Nanoparticle is Used as Template As described below, a mixed self-assembled monolayer (mixed SAMs) having an amino group and a bromo group at the end on a gold thin film deposited glass base plate was produced (molecular film-forming step), an NTA group was introduced into the amino group at the end to form a NTA-Ni complex, then silica nanoparticles were immobilized by chelate bond (template introduction step). Then, the silica nanoparticles were modified with a methacrylic group (surface modification step), and a polymer thin film was synthesized by surface-initiated living radical polymerization (polymerization step). Finally, the silica nanoparticles were removed (removal step) to obtain a base material for producing a sensor for analysis of a detection target.

(1) Formation of Mixed Self-Assembled Monolayer with Bromo Group and Amino Group (Molecular Film-Forming Step)

In the same manner as in Item 1 in Example 1, organic residues in the gold thin film deposited glass base plate were removed and the gold thin film deposited glass base plate was washed, and the base plate was immersed in an ethanol solution of 0.5 mM amino-EG6-undecanthiol hydrochloride and 0.5 mM 2-(2-bromoisobutyryloxy) undecyl thiol and allowed to stand at 25° C. for 24 hours to form a mixed self-assembled monolayer with a bromo group and an amino group.

(2) Immobilization of SH/His-Tagged Silica Nanoparticles Via Ni-NTA (Template introduction step)

A DMSO solution of 5 mM isothiocyanobenzyl-nitrilotriacetic acid (ITC-NTA) (80 µL) was dropped onto the base plate, and the base plate was allowed to stand at 25° C. for 2 hours to modify the amino group with NTA. The base plate was washed with DMSO and pure water, then 100 µL of 4 mM $NiCl_2$ aqueous solution was dropped onto the base plate, and the base plate was allowed to stand at room temperature for 15 minutes to form a Ni-NTA complex. Then, 100 µl of an aqueous solution containing SH/His-tagged silica nanoparticles (solid content concentration: 5.1 mg/ml) was dropped onto the base plate, and the base plate was allowed to stand at 25° C. for 1 hour.

(3) Methacryloylation of Immobilized SH/His-Tagged Silica Nanoparticles (Surface Modification Step)

In 100 µM 2-(2-pyridyl) dithioethyl methacrylate PBS (pH 7.4) solution, the base plate was immersed and allowed to stand overnight to introduce a methacryloyl group via a disulfide into the SH group on the surface of the silica nanoparticles by disulfide exchange reaction.

(4) Production of MIP Thin Film (Polymerization Step)

A polymer thin film was synthesized on the base plate in the same manner as in Item 4 in Example 1 except that the polymerization time was 3 hours. Thus, a polymer thin film in which the methacryloyl group in the silica nanoparticles was also copolymerized together with the monomer in Table 1 was obtained on the base plate. After completion of the polymerization, the base plate was immersed in an aqueous solution of 1 M ethylenediaminetetraacetic acid-4Na for 15 minutes to remove $Cu^{2+}$ used for ATRP.

(5) Removal of Silica Nanoparticles (Removal Step)

The base plate was immersed in an aqueous solution of 50 mM tris (2-carboxyethyl) phosphine/HCl (TCEP) at 25° C. for 3 hours to reduce and cleave the disulfide bond that binds the polymer to silica nanoparticles. Though a free SH group remains on the polymer side, this SH group is derived from SH/His-tagged silica nanoparticles, thus it is not present in the part other than the concave corresponding to the template in the polymer thin film, and it is present only in the concave corresponding to the template. Though it is highly possible that in the above-mentioned EDTA-4Na treatment, the nickel in NI-NTA was also removed and the His-tag became free at that time, the following operation was also performed as a precaution. The base plate was washed with pure water, then the base plate was immersed in 50 mM acetate buffer (pH 4.0) containing 0.5 wt % SDS to wash out silica nanoparticles bound via Ni-NTA and His-tag from the polymer thin film.

Example 9: Sensor for Analysis of Detection Target when Silica Nanoparticle is Used as Template To form Ni-NTA again on the base material for producing a sensor for analysis (MIP base plate) obtained in Example 8, the MIP base plate was treated with an aqueous solution of 4 mM $NiCl_2$. Then, 100 µM His-tag Protein G dissolved in PBS was added to the base plate to immobilize Protein G capable of binding the antibody via His-tag. Finally, 0.3 UM Anti-CD9 antibody dissolved in PBS was added to the base plate to immobilize the Anti-CD9 antibody via Protein G. Because Protein G binds to the Fc region of the antibody, the orientation of the immobilized antibody is uniform.

Further, a fluorescent molecule was selectively introduced into the concave in the sensor for analysis using thiol-reactive Alexa Fluor® 647 $C_2$ Maleimide as the fluorescent molecule. The fluorescence intensity before introduction was 113±0.6 (n–3), and the fluorescence intensity after introduction was 151±2.1 (n–3), confirming the introduction of fluorescence. Thus, the sensor for analysis of a detection target was obtained.

Example 10: Exosome Detection by Fluorescence Analysis Using Sensor for Analysis of Detection Target Using the sensor for analysis (with an antibody) obtained in Example 9, the binding behavior of the exosome was observed. For comparison, the binding behavior of the exosome was also observed in the same manner for the base plate in the sensor for analysis on which the Anti-CD9 antibody was not immobilized (without an antibody). As a sample, PBS (10 mM phosphate, 140 mM NaCl, pH 7.4) solutions of the exosome (concentrations were 0.01, 0.05, 0.1, 0.5, 1, 5, and 10 ng/mL, respectively) were used, and fluorescence detection of the exosome was performed under a microscope. The fluorescence microscope measurement conditions were as follows.

Figure 18:
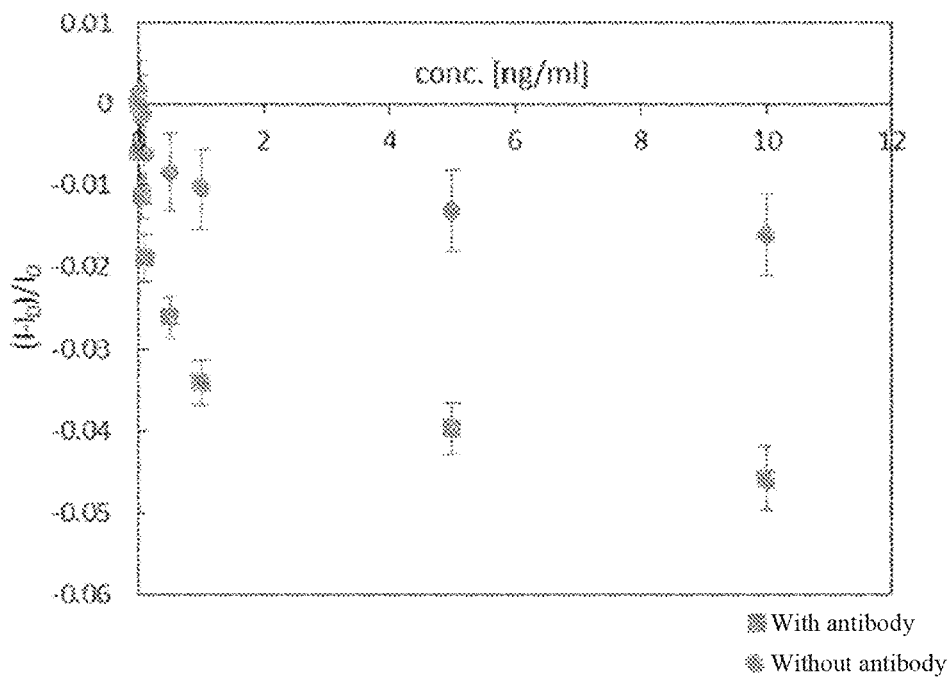
FIG. 18 shows a graph showing the fluorescence intensity change with respect to the exosome concentration, obtained in exosome detection by fluorescence analysis using the sensor for analysis of the present invention (produced using a silica nanoparticle as a template; with an antibody) in Example 10.

Filter: Cy5
Objective lens: ×5
Exposure time: 0.1 sec
Light source: Mercury lamp The results are shown in FIG. 18. In FIG. 18, the horizontal axis indicates the exosome concentration, and the vertical axis indicates the fluorescence intensity change. The dissociation constant calculated from the adsorption isotherm based on the result in FIG. 18 was $K_d$=3.8×10$^{-15}$ [M]. The estimated $M_w$ of the exosome is 2.33×10$^8$ Da, and thus the exosome was successfully detected with excellent sensitivity comparable to that when an exosome was used as a template.

Example 11: STED Super-Resolution Image of Surface of Sensor for Analysis

Figure 19:
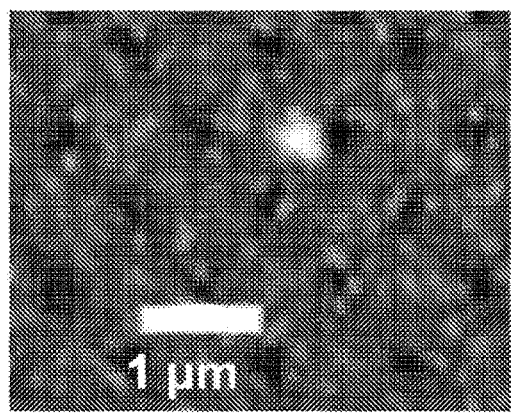
FIG. 19 shows an image obtained by observing the sensor for analysis of the present invention in Example 11 (produced using a silica nanoparticle as a template) using a stimulated emission depletion (STED) microscope.

A sensor for analysis was produced in the same manner as in Example 9 except that (P=O-Rhodol represented by the following formula was used as a fluorescent molecule. The obtained sensor for analysis was observed using a stimulated emission depletion (STED) microscope (SP8-STED3X manufactured by Leica Camera AG). The obtained STED super-resolution image is shown in FIG. 19. As shown in FIG. 19, dot-like fluorescence of about 200 nm size was observed, and the size of the fluorescence was equivalent to the silica nanoparticles used for the template, and confirming that it is a concave formed by the template effect. Background fluorescence was hardly observed in the part other than the concave, and thus it was also shown that the fluorescent reporter molecule was selectively introduced into the concave.

[Chemical Formula 4]

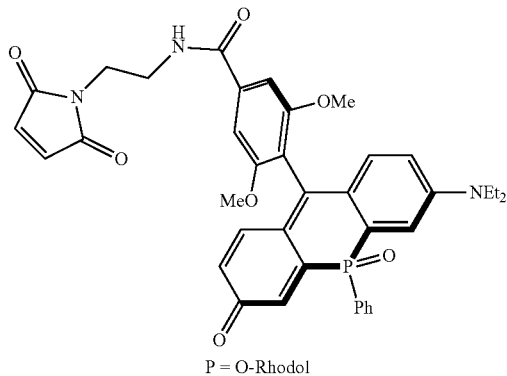

P = O-Rhodol

Example 12: Measurement of Exosome in Tear Fluid

Tear fluid was collected using Schirmer test paper, then the test paper was immersed in 10 mM phosphate buffer (PBS) containing 500 μl of 140 mM NaCl at 4° C. for 6 hours to collect exosomes contained in the tear fluid as a tear fluid sample. The tear fluid sample was subjected to fluorescence measurement using the sensor for analysis in Example 9 to measure exosomes in the tear fluid. For comparison, as a control, the measurement of PBS with the sensor for analysis of a detection target in Example 9, and to confirm the binding of the tear fluid exosome to the antibody of the sensor for analysis, the measurement of the tear fluid sample with a base plate of the sensor for analysis in Example 9 on which the antibody is not immobilized were also performed.

Figure 20:
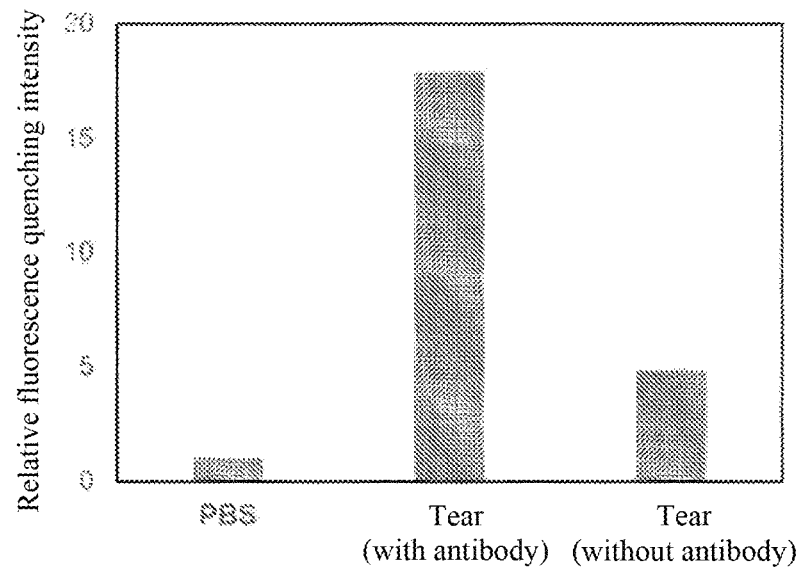
FIG. 20 shows the results of exosome detection in tear fluid using the sensor for analysis of the present invention (produced using a silica nanoparticle as a template) in Example 12.

The results are shown in FIG. 20. In FIG. 20, "PBS" indicates the result of measurement in which PBS was subjected to the sensor for analysis in Example 9, "Tears (with an antibody)" indicates the result of measurement in which the tear fluid sample was subjected to the sensor for analysis in Example 9, and "Tear (without an antibody)" indicates a result of measurement in which the tear fluid sample was subjected to the base plate of the sensor for analysis in Example 9 on which the antibody is not immobilized. As shown in FIG. 20, the degree of fluorescence quenching was largest when the tear fluid sample was subjected to the sensor for analysis in Example 9 on which the antibody was immobilized, and thus it was shown that the exosome in tear fluid was measured.

Though preferred embodiments of the present invention were described above, the present invention is not limited to them, and various other embodiments can be made without departing from the intention of the present invention.

DESCRIPTION OF REFERENCE SIGNS

10: Base material for producing sensor for analysis
20: Base material
21: Molecular film
22: Group for binding antibody substance (Reversible binding group)
22a: Binding functional group
22b: First reversible linked group
22c: Antibody substance-binding group
23a: Polymerization initiating group
24: Antibody substance
25: Group capable of forming first reversible linked group by binding to group for binding antibody substance
30: Polymer film
31: Concave
32: Group for binding signal substance (Reversible binding group)
32b: Second reversible linked group
33: Polymerizable functional group
35: Polymerizable monomer
40: Template
41: Anchoring substance
42: Reversible binding group (Reversible bond group capable of forming second reversible linked group by binding to group for binding signal substance)
43: Anchoring group
50: Sensor for analysis
52: Antibody substance specific to detection target
53: Signal substance
60: Detection target

The invention claimed is:

1. A material for producing a sensor for analysis of a detection target, comprising:
   a base material; and
   a polymer film provided on a surface of the base material,
   wherein the polymer film includes a concave that receives the detection target, and inside the concave is a group for binding an antibody substance and a group for binding a signal substance,
   wherein the group for binding the antibody substance is attached to the base material and is only accessible by the antibody substance through a clearing in the polymer film within the concave, wherein the group for binding antibody substance is a chelate-forming binding group selected from the group consisting of an amino polycarboxylic acid chelating agent-derived group, a hydroxycarboxylic acid chelating agent-derived group, a deferoxamine-derived group, a deferasirox-derived group, a deferiprone-derived group, and a histidine tag, and wherein the amino polycarboxylic acid chelating agent-derived group is selected from the group consisting of ethylenediaminetetraacetic acid (EDTA), ethylenediaminediacetic acid, hydroxyethylethylenediaminetriacetic acid (HEDTA), dihydroxyethylethylenediaminetetraacetic acid (DHEDDA), nitrilotriacetic acid (NTA), hydroxyethyliminodiacetic acid (HIDA), N-(2-hydroxyethyl) iminodiacetic acid, ß-alanine diacetic acid, cyclohexanediaminetetraacetic acid, iminodiacetic acid, N-(2-hydroxyethyl) iminodiacetic acid, diethylenetriaminepentaacetic acid (DTPA), N-(2-hydroxyethyl) ethylenediaminetriacetic acid, glycol ether diamine tetraacetic acid, glutamic acid diacetic acid, aspartic acid diacetic acid, methylglycine diacetic acid, iminodisuccinic acid, serine diacetic acid, hydroxyiminodisuccinic acid, dihydroxyethylglycine, aspartic acid, glutamic acid, and triethylenetetramine-N,N,N',N'',N''',N'''-hexaacetic acid,
   wherein the group for binding the antibody substance is not accessible by the antibody substance on any part of the surface of the base material other than within the concave, and
   wherein the group for binding the signal substance is attached to the polymer within the concave and is not accessible by the signal substance on any part of the polymer film other than within the concave and wherein the group for binding signal substance is a thiol group.

2. The material for producing a sensor for analysis of a detection target according to claim 1, wherein:
   the polymer film is composed of a molecularly imprinted polymer produced using the detection target or an object larger in size than the detection target as a template, and
   the concave corresponds to a part of a surface shape of the template.

3. A sensor for analysis of a detection target, comprising:
   the material for producing a sensor for analysis of a detection target according to claim 1;
   an antibody substance specific to the detection target that is bound to the group for binding antibody substance; and
   a signal substance that is bound to the group for binding signal substance.

4. The sensor for analysis of a detection target according to claim 3, wherein the detection target is a microparticle having a membrane structure.

5. The sensor for analysis of a detection target according to claim 4, wherein the microparticle having a membrane structure is an exosome.

6. The sensor for analysis of a detection target according to claim 3, wherein the antibody substance specific to the detection target has a specific bindability to a specific antigen expressed on a surface of the microparticle having a membrane structure.

7. A method for analyzing a detection target, comprising:
   a step of contacting a sample containing the detection target with the sensor for analysis of a detection target according to claim 3 to bind the detection target to the antibody substance; and
   a step of detecting a change in signal derived from the signal substance.

8. The material according to claim 1, wherein the group for binding an antibody substance specifically binds to an Fc region of the antibody substance.

9. The material according to claim 8, wherein the group for binding an antibody substance comprises Protein G.

* * * * *